US011279936B2

(12) United States Patent
Perlin et al.

(10) Patent No.: US 11,279,936 B2
(45) Date of Patent: Mar. 22, 2022

(54) APTAMERS, BIOSENSORS AND DETECTION METHODS FOR COMMON AZOLE-CLASS ANTIFUNGAL DRUGS

(71) Applicant: Rutgers, The State University of New Jersey, New Brunswick, NJ (US)

(72) Inventors: David S. Perlin, New York, NY (US); Gregory R. Weidman, Union, NJ (US); Yanan Zhao, Livingston, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 220 days.

(21) Appl. No.: 16/637,459

(22) PCT Filed: Aug. 1, 2018

(86) PCT No.: PCT/US2018/044834
§ 371 (c)(1),
(2) Date: Feb. 7, 2020

(87) PCT Pub. No.: WO2019/032347
PCT Pub. Date: Feb. 14, 2019

(65) Prior Publication Data
US 2020/0248182 A1 Aug. 6, 2020

Related U.S. Application Data

(60) Provisional application No. 62/543,077, filed on Aug. 9, 2017.

(51) Int. Cl.
*C12N 15/115* (2010.01)
*G01N 33/53* (2006.01)

(52) U.S. Cl.
CPC ....... *C12N 15/115* (2013.01); *G01N 33/5308* (2013.01); *C12N 2310/16* (2013.01)

(58) Field of Classification Search
None
See application file for complete search history.

(56) References Cited

PUBLICATIONS

GenBank Accession No. CP020784, *Oryzias latipes* strain HNI chromosome 6, Jul. 27, 2017 [online]. [Retrieved on Sep. 10, 2018], Retrieved from the Internet: <URL: <https://www.ncbi.nlm.nih.gov/nuccore/CP020784>> Entire document.
GenBank Accession No. AL592551, Mouse DNA sequence from clone RP23-12113 on chromosome 11, complete sequence, Dec. 13, 2012 [online], [Retrieved on Sep. 10, 2018], Retrieved from the internet: <URL: <https://www.ncbi.nlm.nih.gov/nuccore/AL592551>> Entire document.
GenBank Accession No. JY742591.1, VUK286M08.F VUK *Phaseolus vulgaris* genomic 5', genomic survey sequence, May 9, 2013 [online]. [Retrieved on Sep. 10, 2018]. Retrieved from the internet: <URL: <https://www.ncbi.nlm.nih.gov/nucgss/JY742591>> Entire document.
Wiedman et al. "An aptamer-based biosensor for the azole class of antifungal drugs. mSphere." Aug. 30, 2017, vol. 2, No. 4, p. e00274-17 (pp. 1-10). entire document, especially abstract.
Wiedman et al., Small Molecule Aptamers for Biosensing. Biophysical Journal, Feb. 2017. vol. 112, No. 3, p. 70a. Abstract.

*Primary Examiner* — Tracy Vivlemore
(74) *Attorney, Agent, or Firm* — Fox Rothschild LLP

(57) ABSTRACT

Aptamers having a G-quadruplex structure that bind specifically to the most commonly used azole-class antifungal drugs, biosensors that comprise those aptamers, and invitro methods for determining the level of one of those drugs utilizing those aptamers or biosensors.

11 Claims, 15 Drawing Sheets

Specification includes a Sequence Listing.

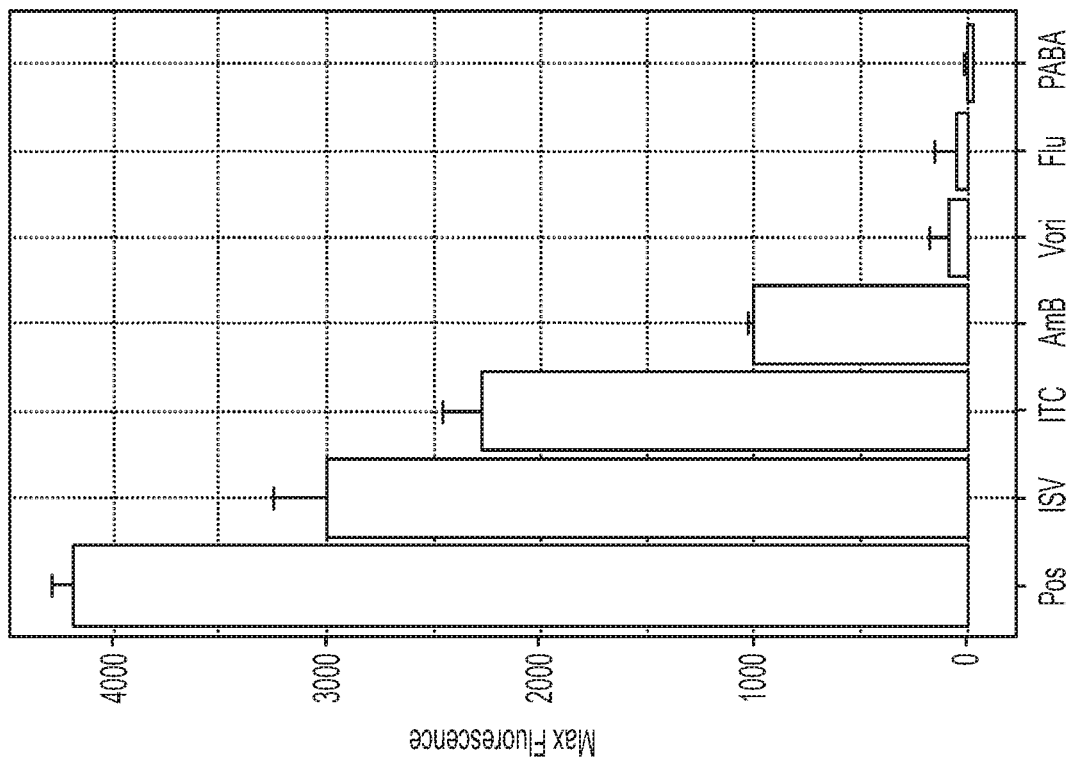
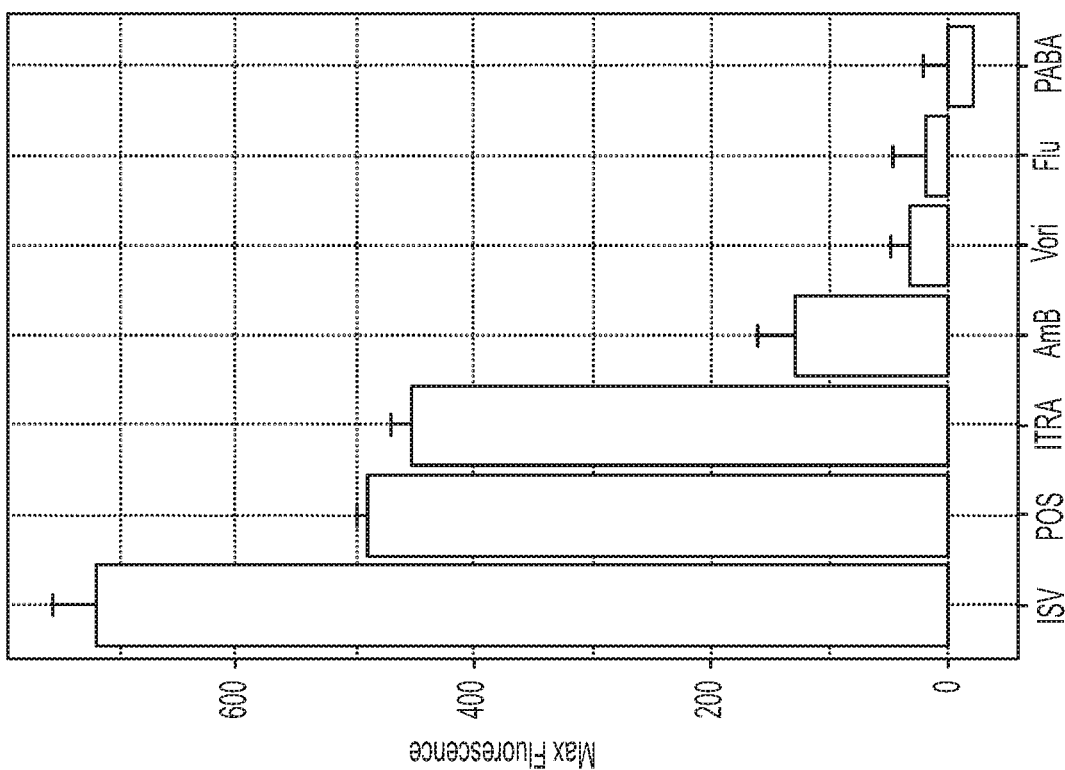
FIG. 13A
FIG. 13B

APTAMERS, BIOSENSORS AND DETECTION METHODS FOR COMMON AZOLE-CLASS ANTIFUNGAL DRUGS

CROSS-REFERENCE TO RELATED APPLICATION

This application claims the benefit of U.S. Provisional Application No. 62/543,077 filed Aug. 9, 2017, the disclosure of which is incorporated herein by reference in its entirety.

CROSS-REFERENCE TO A SEQUENCE LISTING

This application includes a "Sequence Listing" which is provided as an electronic document having the file name "096747.00376_ST25.txt" (2391 bytes, created Jul. 24, 2018), which is herein incorporated by reference in its entirety.

FIELD OF THE INVENTION

This invention relates to the in-vitro detection of the most commonly used azole-class antifungal drugs for treatment or prevention of invasive fungal infection.

BACKGROUND OF THE INVENTION

Understanding a drug's pharmacokinetics is crucial to safely and effectively treating patients. Unfortunately, drug levels in patients can vary significantly, and the factors contributing to this variability are frequently misunderstood. For some critically-ill patients, it is essential to gauge levels of drug in real-time. The best therapeutic management can be achieved by maintaining a therapeutic level in a patient's bloodstream and by optimizing individual dosage regimens. These analyses generally rely upon trough and peak monitoring, and real-time kinetic drug modeling. For this reason, therapeutic drug monitoring (TDM) of some drugs is a critical component of successful therapy. Andes D, Pascual A, Marchetti O (2009) Antifungal Therapeutic Drug Monitoring: Established and Emerging Indications, Antimicrobial Agents and Chemotherapy 53:24-34. It is particularly important to monitor drugs with narrow therapeutic ranges, marked pharmacokinetic variability, target concentrations that are difficult to monitor, and drugs known to cause adverse events.

Azole-class antifungal drugs, the most commonly used members of which are posaconazole, fluconazole, voriconazole and itraconazole, are an important class of lanosterol 14α-demethylase enzyme-inhibiting molecules. Sheehan D J, Hitchcock C A, Sibley C M (1999) Current and emerging azole antifungal agents, Clin Microbiol Rev 12:40-79. These drugs compromise fungal cell membranes by preventing the synthesis of the key component ergosterol. Ghannoum M A, Rice L B. (1999) Antifungal agents: mode of action, mechanisms of resistance, and correlation of these mechanisms with bacterial resistance, Clin Microbiol Rev 12:501-517. A number of these drugs are highly hydrophobic, which creates analytical challenges. Furthermore, because of their hydrophobic nature it is difficult to know how much of the drug is freely available in the blood at any given time. Wide variances in the pharmacokinetics of critically ill patients have been observed for triazole drugs like voriconazole and posaconazole, which has resulted in a need for TDM. Jager N G, van Hest R M, Lipman J, Taccone F S, Roberts J A (2016) Therapeutic drug monitoring of anti-infective agents in critically ill patients, Expert Rev Clin Pharmacol doi: 10.1586/17512433.2016.1172209:1-19. Furthermore, posaconazole and voriconazole have been shown to have drastically different bioavailability depending on how they are administered and if they are co-administered with other drugs Dolton M J, Bruggemann R J, Burger D M, McLachlan A J (2014) Understanding variability in posaconazole exposure using an integrated population pharmacokinetic analysis, Antimicrob Agents Chemother 58:6879-6885; Dolton M J, Mikus G, Weiss J, Ray J E, McLachlan A J (2014) Understanding variability with voriconazole using a population pharmacokinetic approach: implications for optimal dosing, J Antimicrob Chemother 69:1633-1641. Therapeutic drug monitoring in conjunction with antifungal therapy has been shown to promote more favorable outcome compared to non-TDM groups. Park W B, Kim N H, Kim K H, Lee S H, Nam W S, Yoon S H, Song K H, Choe P G, Kim N J, Jang I J, Oh M D, Yu K S (2012) The effect of therapeutic drug monitoring on safety and efficacy of voriconazole in invasive fungal infections: a randomized controlled trial, Clin Infect Dis 55:1080-1087. Unfortunately, TDM requires blood to be drawn from patients and then drug levels in blood evaluated by analytical instrumentation, at some later point in time. Analytical techniques such as Liquid Chromatography and Mass Spectrometry require skilled staff and resources that are not found in all hospitals. Grebe S K, Singh R J (2011) LC-MS/MS in the Clinical Laboratory—Where to From Here? Clin Biochem Rev 32:5-31. These barriers become especially difficult to overcome when treating patients in community hospitals, at home or in resource limited settings. Effective methods for sensing azole-class antifungal drugs in blood samples would make it easier to determine drug concentrations. Any effective TDM method requires a way to capture the drug target from a patient sample. Antibodies provide specificity and sensitivity as a capture probe, but they are typically unstable over a wide range of assay conditions. A more robust alternative is needed.

The compositions and methods of the present invention address and meet these needs.

SUMMARY OF THE INVENTION

One aspect of the present invention relates to a DNA aptamer that has a G-quadruplex structure and binds specifically to posaconazole, fluconazole, isavuconazole, voriconazole and itraconazole, the most commonly used members of azole-class antifungal drugs, wherein the aptamer has a nucleotide sequence consisting essentially of the following regions: a first conserved region consisting essentially of SEQ ID NO: 1, a variable connector region of at least one nucleotide, a second conserved region consisting essentially of SEQ ID NO: 2, and a variable 3' terminal region of 0-10 nucleotides, said aptamer having a binding affinity for posaconazole of at least 50% of the binding affinity of aptamer SEQ ID NO: 4 (also referred to herein as "Rd 13", "RD 13", "Rd13", "aptamer Rd13" and "Rd13 aptamer") as determined by a change in anisotropy upon titration of 100 pmoles of aptamer into 100 pmoles of BODIPY-labeled posaconazole.

This invention includes DNA aptamers for the most commonly used azole-class drugs, namely, posaconazole, fluconazole, voriconazole, and itraconazole. An aptamer according to this invention has a G-quadruplex structure, binds specifically to the azole-class antifungal drugs posaconazole, fluconazole, voriconazole, isavuconazole, and itraconazole, and it has a nucleotide sequence consisting essentially of the following four regions in order 5' to 3': a first conserved region consisting essentially of the sequence CGGGGGGAGGCGGAGGGAGGACTGGG (SEQ ID NO: 1), a variable connector region of at least one nucleotide, a second conserved region consisting essentially of the sequence GGGGTAAGGGCTTAGGTGGTTGG (SEQ ID NO: 2), and a variable 3' terminal region of 0-10 nucleotides. An aptamer according to this invention has a binding affinity for posaconazole of at least 50% of the binding affinity of aptamer Rd 13, which has the sequence CGGGGG-GAGGCGGAGGGAGGACTGGGGCTTCAT-TGACGTTCTTCACAGTA GGGGTAAGGGCT-TAGGTGGTTGGTGCCTG (SEQ ID NO: 4) (also referred to herein as "Rd 13", "RD 13", "Rd13", "aptamer Rd13" and "Rd13 aptamer") as determined by a change in anisotropy upon titration of 100 pmoles of aptamer into 100 pmoles of BODIPY-labeled posaconazole.

The first and second conserved regions, SEQ ID NOS: 1 and 2, individually form G-tetrads and together fold into an intramolecular G-quadruplex structure. These regions are "conserved", meaning that limited changes (additions, subtractions and substitutions) are permitted only insofar as G-tetrad and G-quadruplex structures are maintained. That is not the case for the variable regions, which can vary both in length and nucleotide sequence and still permit the molecule to fold into a G-quadruplex structure. Aptamers according to this invention include, for example, molecules in which the variable connector region is a shortened version of the sequence of the variable connector region of aptamer Rd 13, including aptamer Rd 13 T6: CGGGGGGAGGCG-GAGGGAGGACTGGG GCTTGAGGGGTAAGGGCTTAGGTGGTT GGTGCCTG (SEQ ID NO: 5), wherein the six nucleotides (GCTTGA) of the variable connector region are underlined; and Rd 13 T1: CGGGGGGAGGCGGAGGGAGGACTGGG TGGGGTAAGGGCTTAGGTGGTTGGTGC CTG (SEQ ID NO: 6), wherein the single nucleotide of the variable connector region is underlined. Each of aptamer RD 13 T6 and aptamer Rd 13 T1 and has a binding affinity for posaconazole greater than 50% of the binding affinity of aptamer Rd 13, and thus is an aptamer according to this invention. The 3' region may contain 0-10 nucleotides to assist further functionalization provided that the G-quadruplex structure of the aptamer is not disrupted. Certain preferred aptamers have sequences that include SEQ ID NO: 1 as the first conserved region and SEQ ID NO: 2 as the second conserved region. In one embodiment, a DNA aptamer is SEQ ID NO: 4.

As stated above, an aptamer according to this invention consists essentially of the four defined sequences. It may include additionally a substance, bound thereto by covalent or non-covalent bonds, that imparts additional functionality, including capture and detection, as long as the specific binding to the identified common azole drugs is not materially adversely affected. Examples of such substances include polynucleotides, biotin, streptavidin, and fluorescent substances such as fluorophores. Any suitable detectable labels, including fluorescent labels (fluorophores), can be used. Several suitable fluorophores are described in U.S. patent application Ser. No. 14/399,772, and U.S. Pat. No. 9,700,638, both of which are incorporated herein by reference. One example of such a fluorescent label (fluorophore) is boron-dipyrromethene (BODIPY), or derivative thereof. Also, the molecule may include an amino group for fixing the aptamer molecule to a surface.

Another aspect of this invention is a biosensor comprising the foregoing aptamer affixed to the surface of a material, for example, a solid surface of a graphene field effect transistor (GFET). The biosensors of the present invention are for in vitro detection of azole class drugs posaconazole, fluconazole, voriconazole, isavuconazole, and itraconazole in a sample. The biosensors described herein provide enhanced specificity and lower toxicity than known biosensors. As used in this description, including the appended claims, the term "biosensor" is used in a broad sense of an aptamer attached to the surface of a material so as to be immobilized thereon. The material may be, for example, a solid-phase carrier such as a magnetic bead, a microfluidic chip or a reaction chamber; or an electrical or electronic device such as a metallic (for example, gold) electrode whose impedance increases as drug concentration increases, or a transistor. Attachment may be by any suitable means, including covalent or non-covalent bonding, directly or through a linker. Currently our preferred biosensor is a graphene field effect transistor (GFET) having an aptamer according to this invention fixed to its surface by a linker.

Yet another aspect of this invention is an in vitro method for detecting one of the most commonly used azole-class antifungal drugs in a sample comprising adding to a sample suspected to contain at least one such azole-class antifungal drug a DNA aptamer or biosensor according to this invention and detecting the level of binding of the aptamer to the drug, either by detecting the amount of aptamer bound or by detecting the binding strength of the aptamer to the drug.

This invention also includes methods for in vitro measurement of the amount of an azole-class drug selected from the group of posaconazole, fluconazole, voriconazole, isavuconazole, and itraconazole in a biological sample. Such methods include contacting an aptamer or biosensor of this invention to a sample, for example, a blood sample obtained from a human, forming a complex between the aptamer and the drug, and detecting the level of binding, either by measuring the binding strength of the aptamer to the drug or the amount of aptamer that is bound to the drug. For example, the aptamer can be a substitute for an antibody against the drug in an immunological method such as enzyme immunoassay (EIA), for example, an ELISA method or fluorescent immunoassay (FIA). Western blot techniques, immunohistochemical staining and cell sorting can be included, as can surface plasmon resonance (SPR). Such methods may also include using a biosensor having the aptamer affixed to its surface to capture the drug and measuring an electrical change; for example, capturing the drug with the aptamer bound to an electrode and measuring the change in impedance due to the presence of the drug, or capturing the drug with the aptamer fixed to the surface of a GFET and measuring the Dirac voltage shift. Some methods may include the use of a calibration curve for quantitation.

As used herein the terms "sample" and "biological sample" are used interchangeably and mean a material which can be specifically related to a patient and from which specific information about the patient can be determined, calculated or inferred. A sample can be composed in whole or in part of biological material from of the patient. An example of a biological sample is a biological fluid. Non-limiting examples of biological fluids include blood, serum, serosal fluids, plasma, lymph, urine, cerebrospinal fluid, saliva, mucosal secretions of the secretory tissues and organs, vaginal secretions, breast milk, and tears. Additional examples include fluids of the pleural, pericardial, peritoneal, abdominal and other body cavities, and the like.

Biological fluids may further include liquid solutions contacted with a subject or biological source, for example, cell and organ culture medium including cell or organ conditioned medium, lavage fluids and the like. The aptamers, biosensors, assays and methods described herein can be used to analyze any biological sample.

BRIEF DESCRIPTION OF THE FIGURES

FIG. 13A and FIG. 13B are a pair of graphs showing aptamer release from the rGO surface caused by drugs, as determined by fluorescence values, which was measured in SELEX buffer (13A) and in SELEX buffer +10% Serum (13B). The long tailed azole class drugs posaconazole, isavuconazole, and itraconazole, liberated the greatest amount of aptamer. Polyene drugs (Amphotericin B), the compact azole drugs voriconazole and fluconazole, as well as the drug para-aminobenzoic acid elicited little amounts of aptamer release.

DETAILED DESCRIPTION OF THE INVENTION

Figure 1:
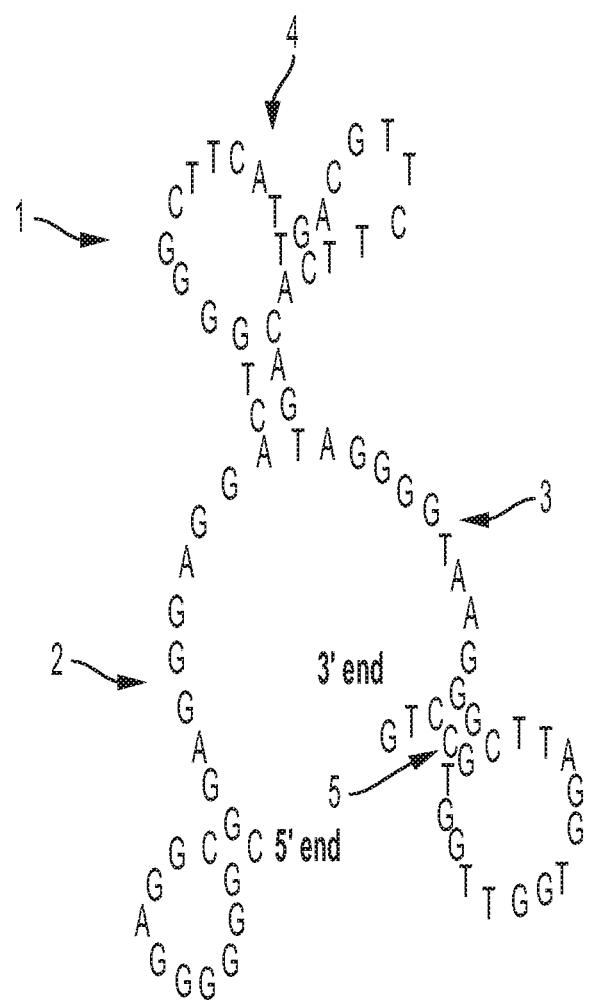
FIG. 1 is a schematic diagram of the predicted secondary structure of aptamer Rd 13 (1) (SEQ ID NO: 4).

Synthesized aptamer Rd 13 (SEQ ID NO: 4) was analyzed by QGRS mapping to predict the existence of G-quadruplex structure. It was found to contain two regions of predicted G-quadruples structure. See, Lea W A, Simeonov A (2011) Fluorescence polarization assays in small molecule screening, Expert Opin Drug Discov 6:17-32. Those G-quadruple structure regions are SEQ ID NO: 1 and SEQ ID NO: 2. Stem-loop structure-predicting software was used to map the room temperature (298° K) structure of the aptamer. See Jing M, Bowser M T (2011) Methods for measuring aptamer-protein equilibria: a review, Anal Chim Acta 686: 9-18. The predicted sequence (consensus sequence) and structure of aptamer Rd 13 (1) is shown in FIG. 1. It will be noted that aptamer Rd 13 forms a stem-loop structure with two separate arms, one of which includes SEQ ID NO: 1 ((2) in FIG. 1, referred to as region 2) and the other of which includes SEQ ID NO: 2 ((3) in FIG. 1, referred to as region 3). FIG. 1 presents the sequence (SEQ ID NO: 4) and predicted structure of molecule 1 (aptamer Rd 13-(1) in FIG. 1). Nucleotides 1-26 constitute SEQ ID NO: 1, nucleotides 51-73 constitute SEQ ID NO: 2, nucleotides 27-50 (GCTT-CATTGACGTTCTTCACAGTA (SEQ ID NO: 3) ((3) in FIG. 1) constitute the variable connector region 4 ((4) in FIG. 1), and nucleotides 74-79 (TGCCTG) constitute the variable 3' terminal region 5 ((5) in FIG. 1). As described above, aptamer Rd 13 T6 includes a variable connector region 4 of only six nucleotides (GCTTGA). Also as described above, aptamer Rd 13 T1 includes a variable connector region 4 of a single nucleotide, which is a thymine (T) (nucleotide 49 in SEQ ID NO: 4). In an embodiment, the sequence of a DNA aptamer as described herein is:

CGGGGGGAGGCGGAGGGAGGACTGGGN$_{(0\text{-}24)}$ GGGGTAAGGGCTTAGGTGGTTGGN$_{(0\text{-}6)}$ (SEQ ID NO: 8), wherein N is any of A, T, G, or C. In this sequence, "N$_{(0\text{-}24)}$" means that there are any number of 0 to 24 nucleotides at that position (wherein N is any of A, T, G or C). Also in this sequence, "N$_{(0\text{-}6)}$" means that there are any number of 0 to 6 nucleotides at that position (wherein N is any of A, T, G or C).

Figure 2:
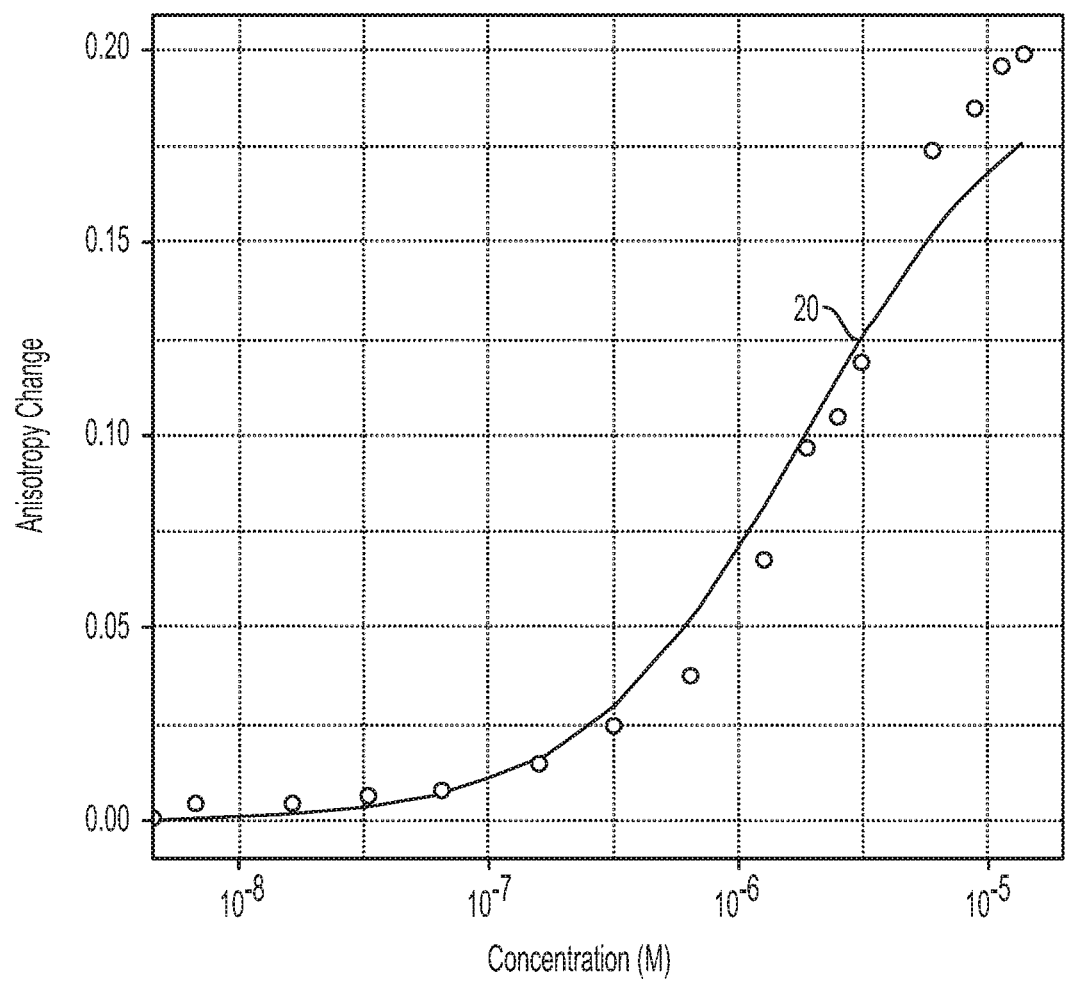
FIG. 2 is a graph of the change in anisotropy versus the concentration of aptamer Rd 13 added to 100 pmoles of BODIPY-labeled posaconazole.

Fluorescence anisotropy experiments, reported below in Example 1, were used to determine the dissociation constants for the posaconazole-aptamer complex. See Lea and Simeonov, and Jing and Bowser, supra. These experiments measured the ability of a BODIPY-labeled posaconazole (PosBD) to rotate in solution. Inhibited rotation, due to aptamer binding, was detected as a change in anisotropy relative to starting anisotropy. In these experiments aptamer Rd 13 caused an increase in anisotropy from titrations of a constant PosBD concentration with increasing amounts of the aptamer (FIG. 2). The dissociation constant when fitting to the fraction bound was found to be 2.7±1.2 μM. We note that the overall dissociation constant for PosBD might be weaker than that of unlabeled posaconazole.

Figure 3:
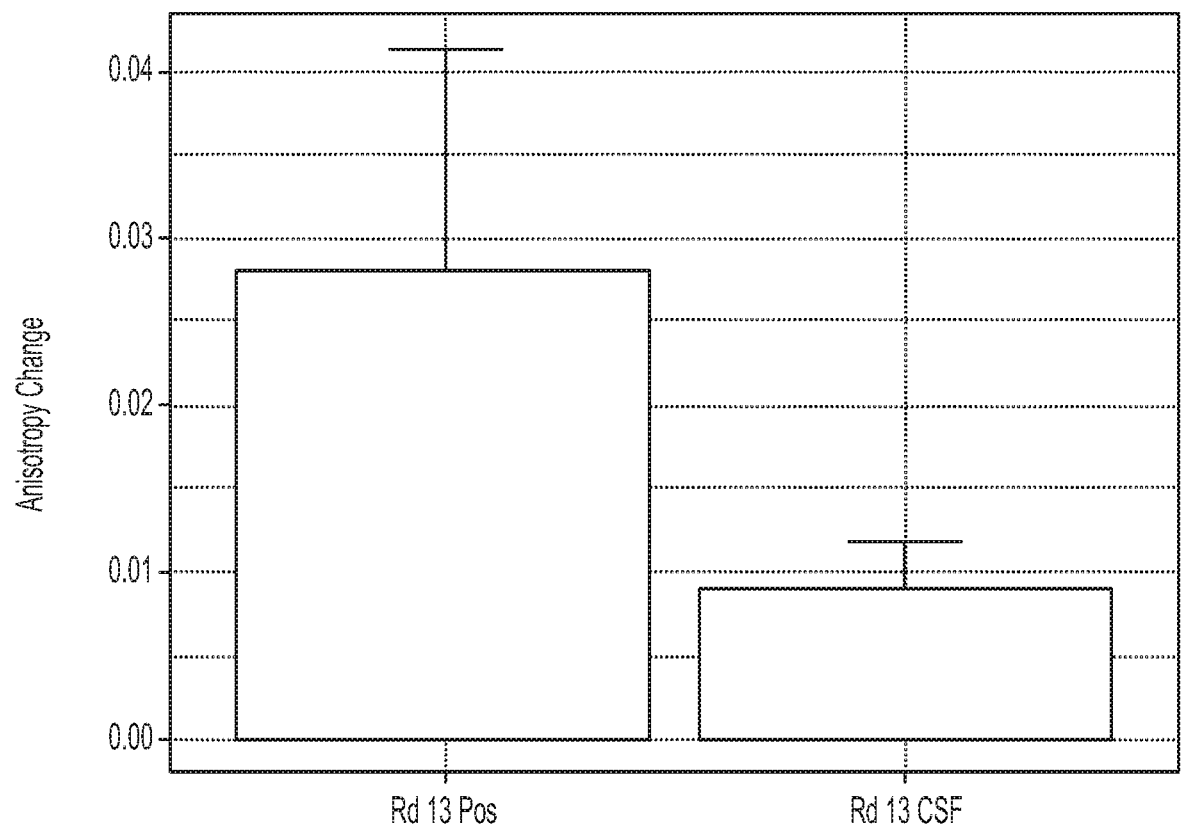
FIG. 3 is a bar graph showing the change in anisotropy caused by adding aptamer Rd 13 to fluorescently labeled posaconazole or caspofungin.

Anisotropy changes were further used, as also reported in Example 1, to probe the specificity of aptamer Rd 13 for the target PosBD. Specificity was also investigated with respect to another BODIPY-labeled molecule: caspofungin (Csf), an echinocandin class drug that is chemically dissimilar to toposaconazole. As reported in Example 1 and shown in FIG. 3, titrating 100 pmoles of Rd 13 aptamer into a 125 µL solution containing 100 pmoles of PosBD causes a much greater anisotropy change than titrating the aptamer into 100 pmoles of CsfBD.

Figure 4:
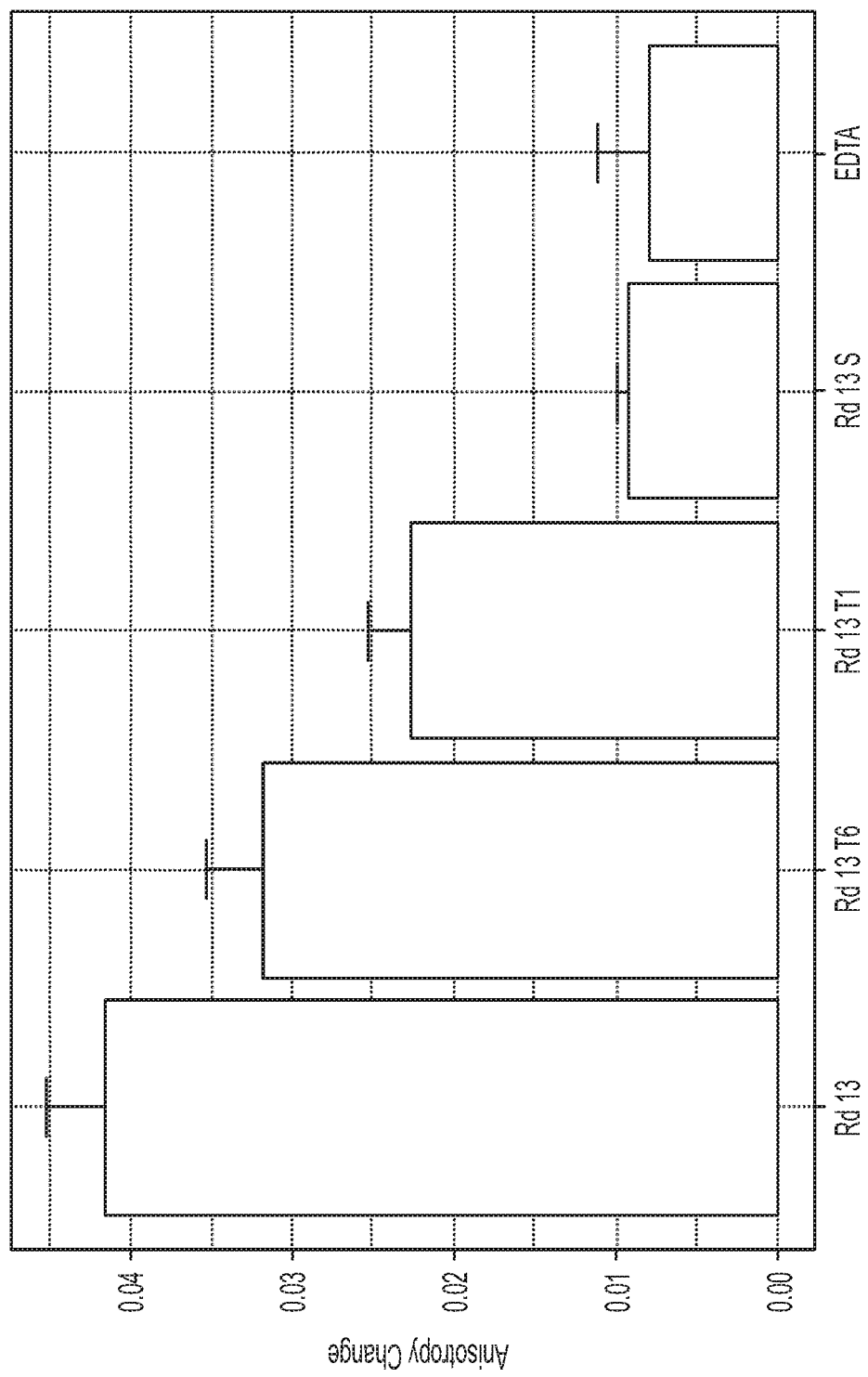
FIG. 4 is a bar graph showing the change in anisotropy caused by adding fluorescently labeled posaconazole one of aptamers Rd 13, Rd 13 T6 or Rd 13 T1; or molecule Rd 13 S; or EDTA.

As also reported in Example 1, the anisotropy change caused by aptamer Rd 13 was compared to the anisotropy changes caused by truncated versions Rd 13 T6 (SEQ ID NO: 5) and Rd 13 T1 (SEQ ID NO: 6) by titrating 100 pmoles of each into 100 pmoles of PosBD. The results, shown in FIG. 4, reveal that the anisotropy change caused by Rd 13 T6 was approximately 75% of the change caused by aptamer Rd 13, and the anisotropy change caused by Rd 13 T1 was approximately 54% of the change caused by aptamer Rd 13. Based on these results, Rd 13 T6 and Rd 13 T1 were judged to be aptamers according to this invention. The anisotropy changes caused by a version of molecule Rd 13 in which the order of nucleotides was jumbled (referred to as scrambled molecule Rd 13 S) and by EDTA were also compared to the anisotropy change caused by aptamer Rd 13. As shown in FIG. 4, the scrambled molecule Rd 13 S did not cause a significant anisotropy change compared to a control such as EDTA and hence did not bind to PosBD and is not an aptamer according to this invention. These results indicate that the G-quadruplex structure, which is missing for Rd 13 S, is necessary for binding, thereby showing that the first region of aptamer Rd 13 is a conserved region for which additions, subtractions and substitutions are quite limited. The results of Example 1 presented in FIG. 4 demonstrate that the connector region of aptamer Rd 13 is a variable region for which additions, subtractions and substitutions are freely permitted as long as the molecule folds into a G-quadruplex structure.

Figure 5:
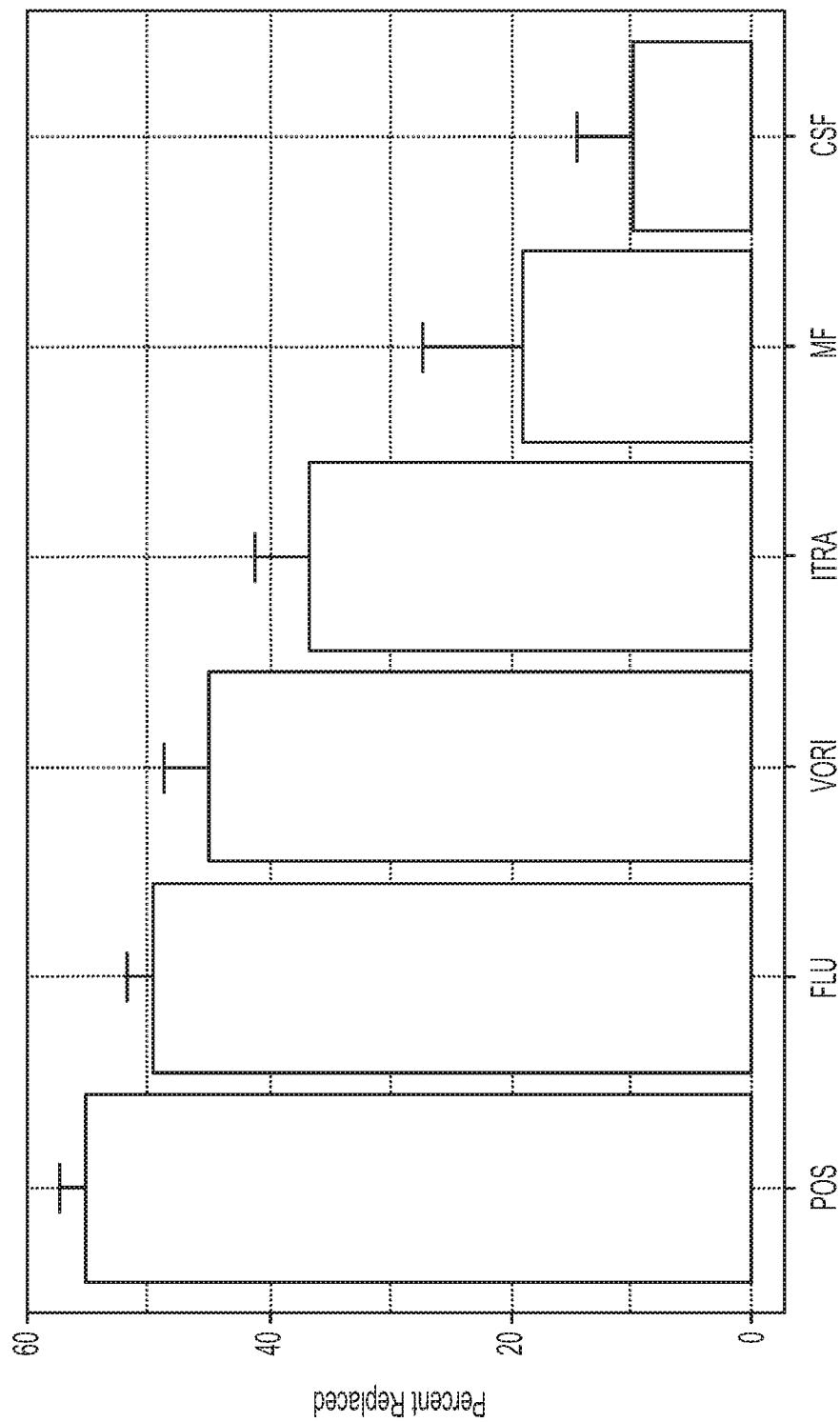
FIG. 5 is a bar graph showing the amount of fluorescently labeled drugs that were replaced by unlabeled drugs in the competition assay of Example 2.

The aptamers of this invention bind to azole-class antifungal drug targets, specifically to those with the exposed terminal azole group like posaconazole. High specificity is important for downstream diagnostic devices to prevent false positive readings. The anisotropy experiments discussed above were modified slightly to develop a competitive assay to further probe specificity. This procedure, described below in Example 2, shows the relative ability of various drugs to replace PosBD in a complex with an aptamer according to this invention, namely, aptamer Rd 13. The replacement ability of several unlabeled drugs was tested: azole-class drugs posaconazole (Pos), fluconazole (Flu), Itraconazole (Itra) and voriconazole (Vori); and chemically distinct echinocandin antifungal drugs micafungin and caspofungin. The percent replacement by each of those drugs is shown in FIG. 5. As shown in FIG. 5, posaconazole displaced the greatest amount of PosBD, that is, more than half of the PosBD (approximately 55%). Closely related azole drugs fluconazole and itraconazole replaced somewhat fewer PosBD molecules, approximately 45-50%. The less closely related azole drug itraconazole replaced fewer PosBD molecules, but still approximately 35%. The chemically distinct echinocandin antifungal drugs micafungin and caspofungin had little effect, replacing fewer than 20% of PosBD molecules. Of the azole drugs, itraconazole is the most hydrophobic. The lower amount of PosBD replacement with itraconazole compared to posaconazole indicates that binding is not solely driven by hydrophobic effects, and that secondary structure plays a large part in the binding of azole targets to aptamers of this invention. Posaconazole and the other commonly used azole class antifungal drugs to which aptamers of this invention bind specifically exhibit strong hydrophobicity (for example, a CLOGP of −4.11 for posaconaxole) and protein binding (for example, >98% for posaconazole). Despite this fact, aptamers of this invention bind specifically to such azole drugs.

Figure 6:
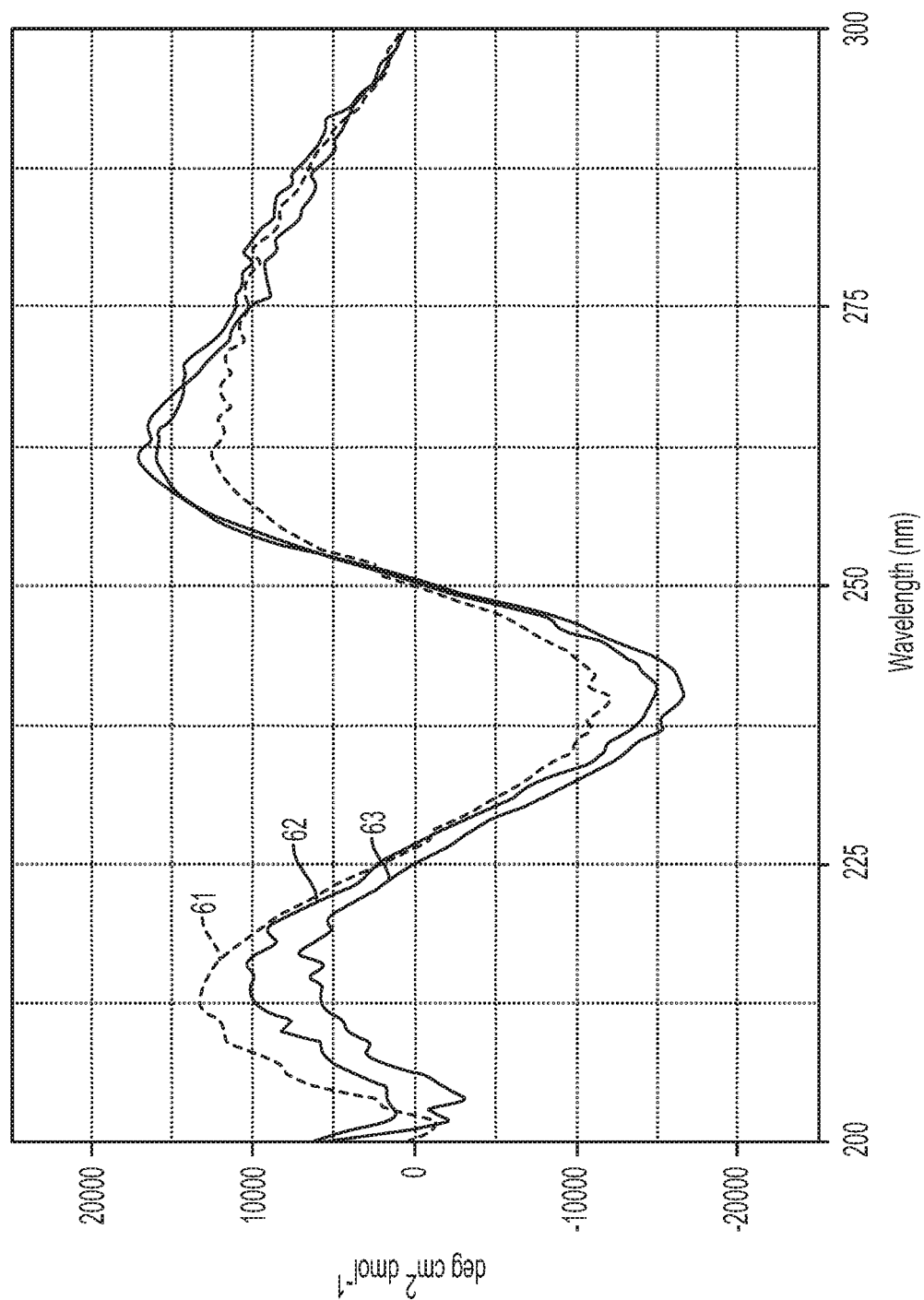
FIG. 6 is a graph of circular dichroism versus wavelength for aptamer Rd 13 in the presence of differing amounts of magnesium chloride.

Circular Dichroism (CD) Spectroscopy experiments were conducted to probe the folding of aptamers of this invention in the presence of salts and posaconazole. The experiments are described in Example 3, and results are presented in FIG. 6. Secondary structure controls the complexing of aptamers and target molecules. As aptamers of this invention contain multiple stretches of guanine (G) residues, we postulated that they form G-quadruplex structures. The CD spectra of aptamer Rd 13 in Tris buffer alone and with the addition of amounts of magnesium chloride from 0 to 1 mM are presented in FIG. 6. The CD spectra of Rd 13 are characteristic of G-quadruplex folded DNA with a maximum at 260 nm and a minimum at 240 nm (FIG. 6). See Paramasivan S, Rujan I, Bolton P H (2007) Circular dichroism of quadruplex DNAs: applications to structure, cation effects and ligand binding, Methods 43:324-331: and Nagatoishi S, Tanaka Y, Tsumoto K (2007) Circular dichroism spectra demonstrate formation of the thrombin-binding DNA aptamer G-quadruplex under stabilizing-cation-deficient conditions, Biochem Biophys Res Commun 352:812-817. Addition of magnesium chloride to the solution both increases the signal at 260 nm and decreases the signal at 240 nm. This indicates that the aptamer forms a G-quadruplex structure in low salt buffer, which is slightly enhanced with the addition of salts.

Figure 7:
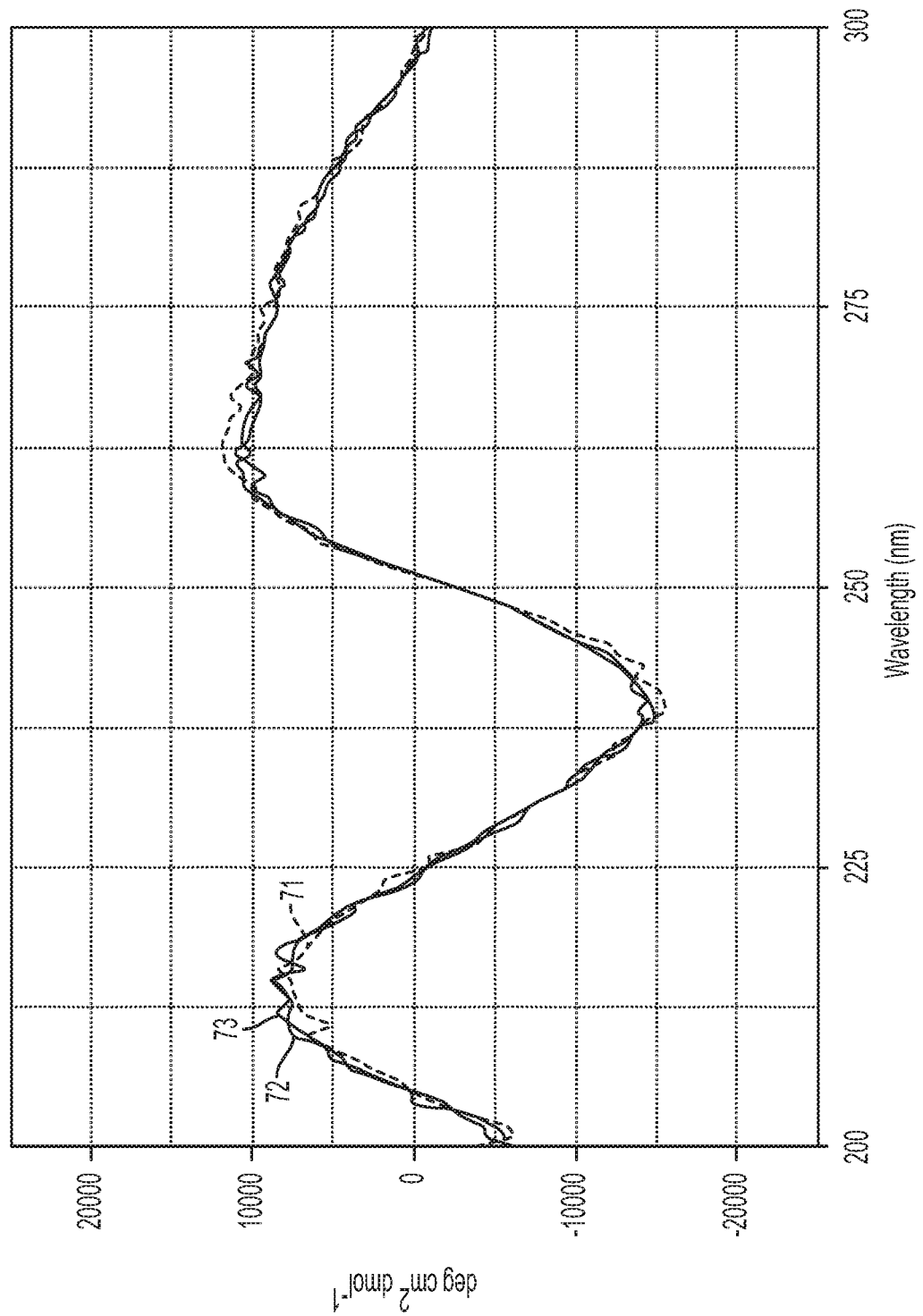
FIG. 7 is a graph of circular dichroism versus wavelength for aptamer Rd 13 in the presence of differing amounts of posaconazole.

Also as reported in Example 3, we obtained CD spectra of aptamer Rd 13 in Tris buffer alone and with the addition of amounts of posaconazole from 0.5 µM to 1 µM. The spectra are presented in FIG. 7. Comparing the spectra in FIGS. 6 and 7, we observed that, in contrast to adding magnesium choloride, the signal is not altered significantly by adding posaconazole in the absence of divalent salts.

Further as also reported in Example 3, we obtained CD spectra of aptamer Rd 13 and molecule Rd 13 scrambled (Rd 13 S) in Tris buffer containing 0.2 mM magnesium chloride. The spectra are presented in FIG. 8, which shows that a G-quadruplex structure formed with aptamer Rd 13 but not with the molecule Rd 13 scrambled.

Figure 8:
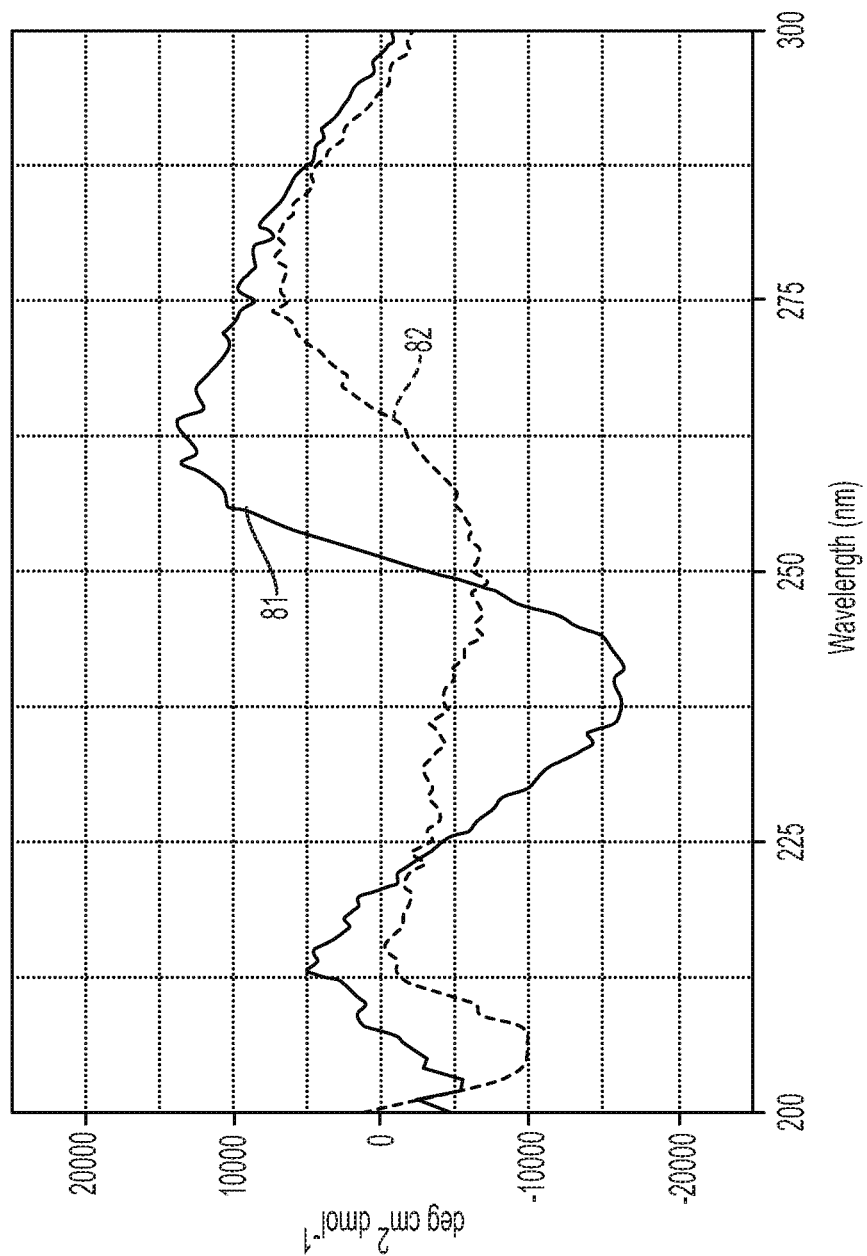
FIG. 8 is a graph of circular dichroism versus wavelength for aptamer Rd 13 and for molecule Rd 13 S in the presence of magnesium chloride.
Figure 9:
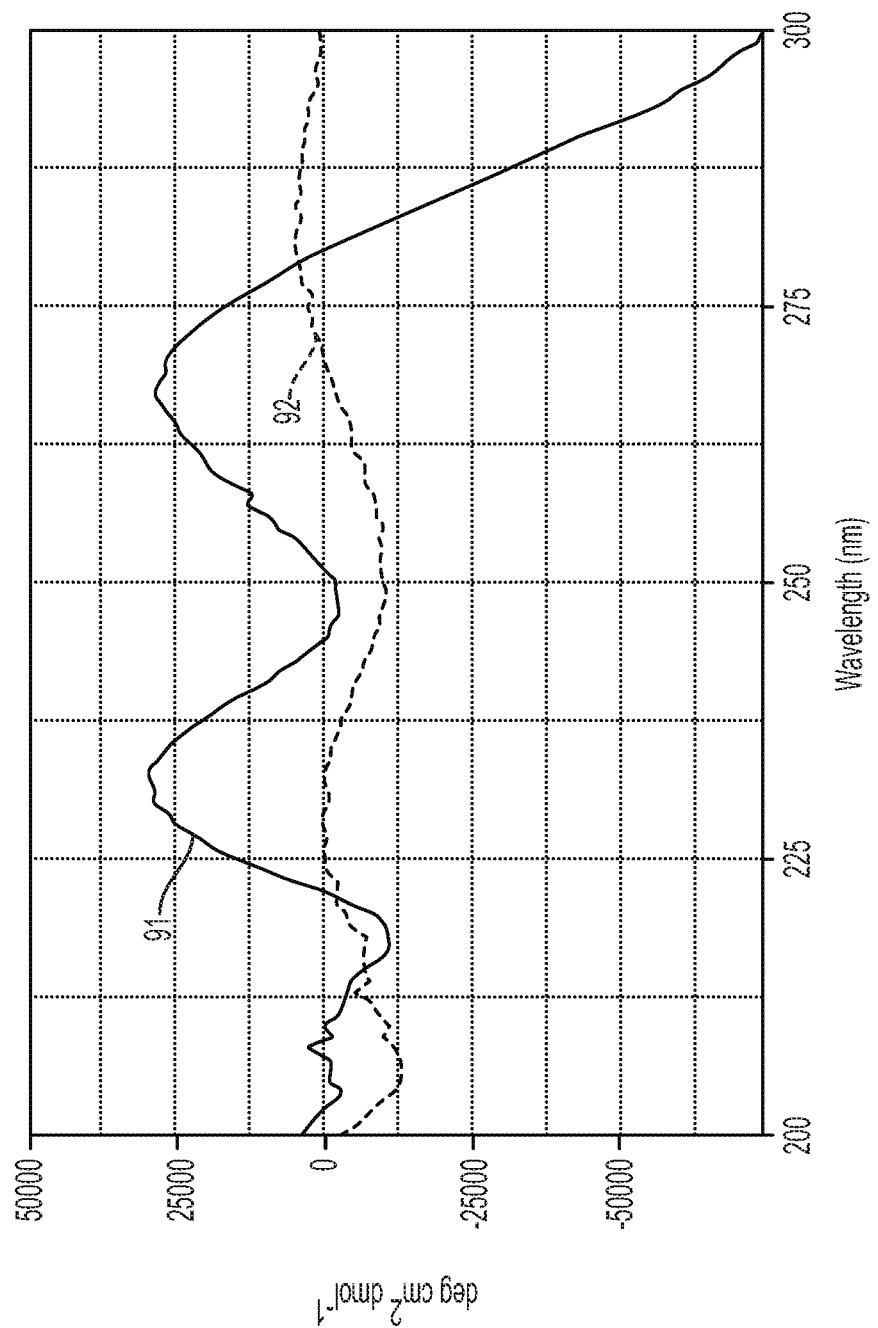
FIG. 9 is a graph of circular dichroism versus wavelength for aptamer Rd 13 and for molecule Rd 13 S in the presence of both posaconazole and magnesium chloride.

As reported in Example 4, we obtained CD spectra of aptamer Rd 13 and molecule Rd 13 scrambled in Tris buffer containing both 0.2 mM magnesium chloride and 100 µM posaconazole. The spectra are presented in FIG. 9. The most drastic change occurs when an aptamer of this invention is exposed to a combination of both posaconazole and salts. Comparing the spectra of FIG. 9 to the spectra of FIG. 8, we observed that when 100 µM posaconazole was added there was a change in the CD signal for aptamer Rd 13. With posaconazole, the spectrum for Rd 13 changes to contain two maxima at about 230 nm and 270 nm with a minimum above 300 nm. In contrast, molecule Rd 13 S did not undergo any further change in secondary structure. Together the results depicted in FIG. 8 and FIG. 9 show that the G-quadruplex structure of aptamer Rd 13 forms in the presence of a divalent salt and that this structure then changes when the target azole class drug is added.

Finally, as reported in Example 5, a new method (assay) using reduced Graphene oxide (rGO) and a fluorescently-labeled aptamer can accurately assess clinically relevant concentrations of posaconazole in little more than one hour from several drops of blood. This method uses the azole class antifungal aptamer to detect posaconazole and itraconazole in human serum samples, e.g., uses rGO and a fluorescently labeled aptamer to detect free drug concentrations. Fluorescein-labeled aptamers are quenched by rGO in the absence of their target. Addition of the target molecules posaconazole and itraconazole liberates the aptamer from the surface, which causes an increase in the fluorescent signal. This signal was then used to generate concentration curves from human serum samples spiked with drug. Assays were performed in human serum diluted to 50% serum and 10% serum. The concentrations, when adjusted for dilution, were found to be within clinically relevant trough concentrations in clinical studies $(C_{min})^{12}$. This assay provided a much-needed way of quickly and accurately monitoring free-drug concentrations of posaconazole and itraconazole. As further described in Example 5, we detected posaconazole and itraconazole in human serum samples (diluted to 50% and 10%); determined a dynamic range detection of posaconazole in 10% serum (0.224 µM to 28 µM); demonstrated selectivity for isavuconazole and itraconazole (vs other hydrophobic drugs); determined a detection limit for posaconazole in 10% serum (0.224 µM); determined a detection limit for isavuconazole in 10% serum (1.12 µM); and determined a detection limit of rGO-aptamer assay for posaconazole in sheep's blood (0.224 µg/mL-upper limit 140 µg/mL).

Figure 10:
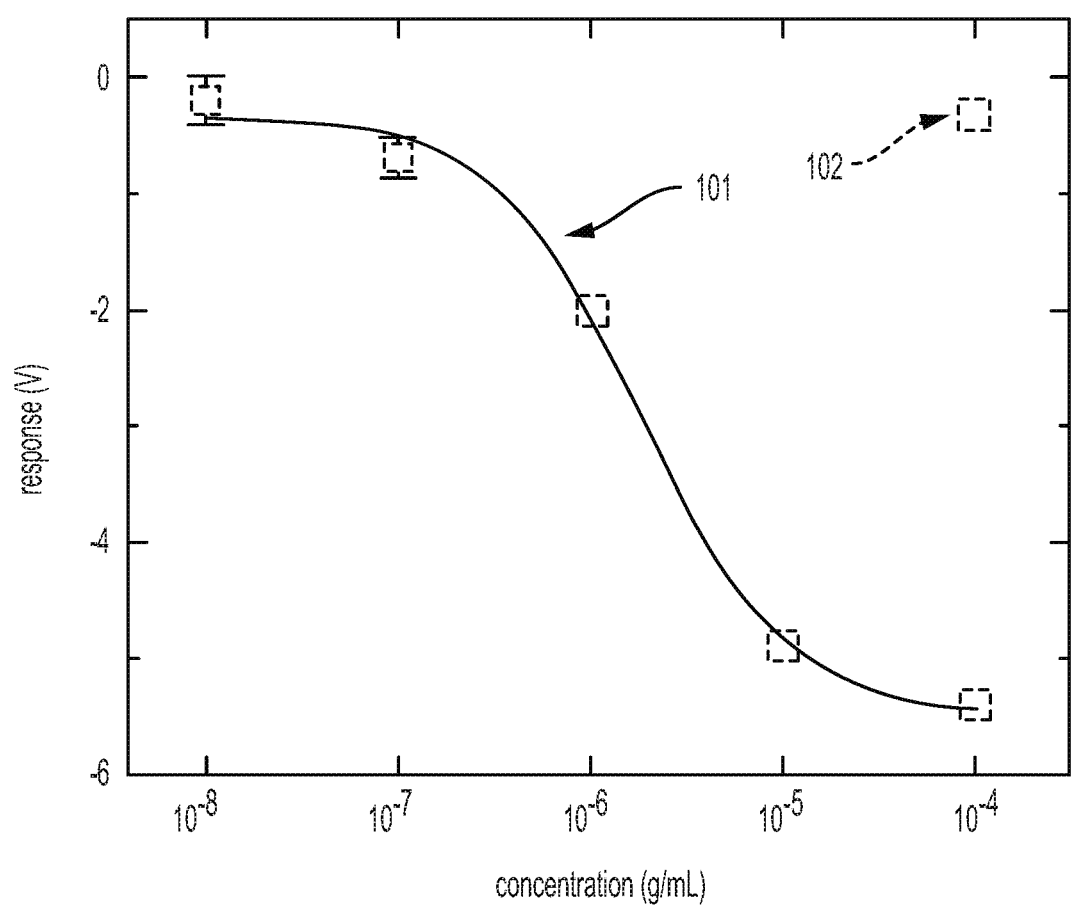
FIG. 10 is a graph of Dirac voltage shift versus drug concentration for the experiment described in Example 4.
Figure 11:
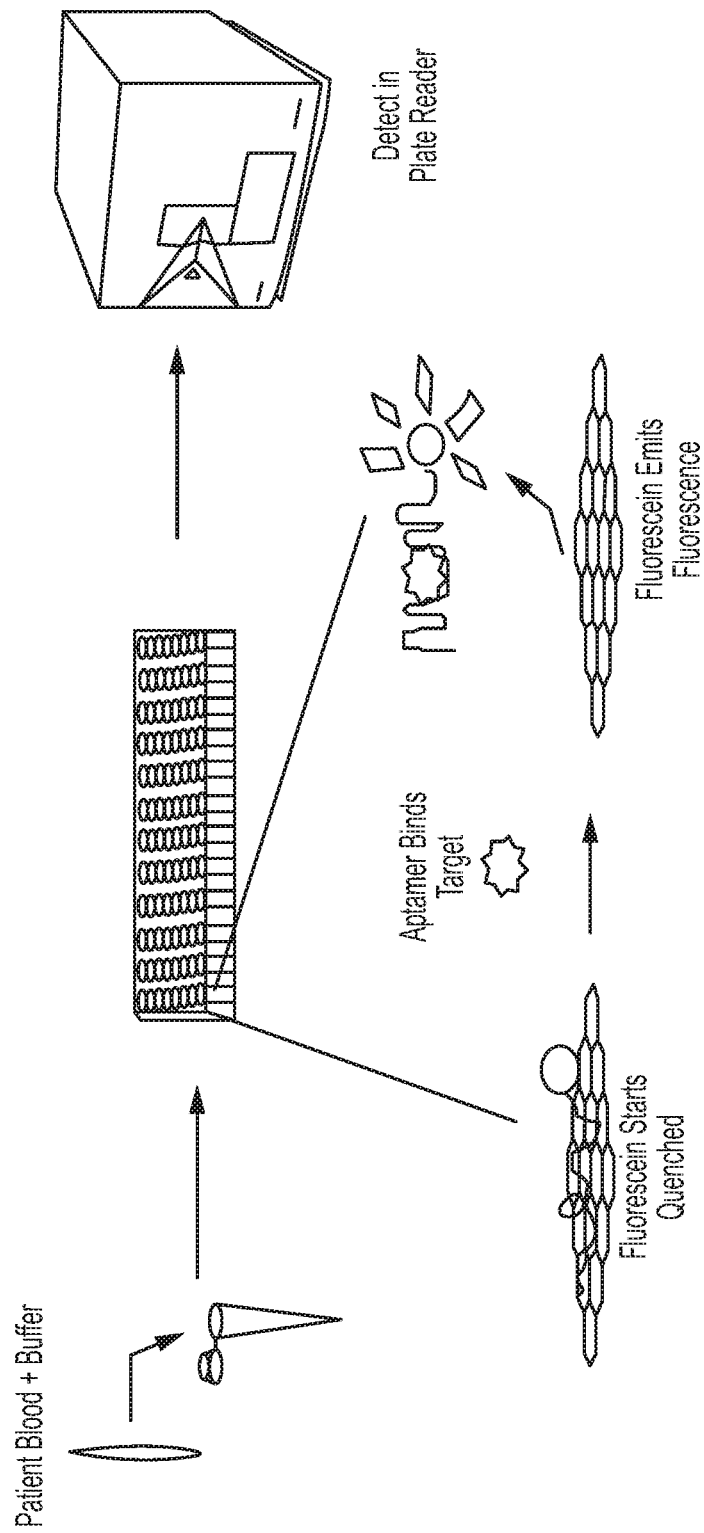
FIG. 11 is a schematic illustration of an embodiment of a method to monitor an azole-class antifungal in human samples.

As an embodiment of a biosensor according to this invention containing a surface to which to affix an aptamer according to this invention, we selected aptamer Rd 13 fixed to the solid surface of a grapheme derivative, namely, a graphene field effect transistor. Graphene Field Effect Transistors (GFET) are a robust platform for detecting the binding of small molecules to a surface. See Schwierz F (2010) Graphene transistors, Nature Nanotechnology 5:487-496. As a transistor, GFETs allow for the flow of charge between a gate and a source over a single sheet of carbon atoms. This sheet is extremely sensitive to changes or binding above it, seen as a change in the Dirac Voltage needed for charge to flow. When combined with GFET devices, the above-described aptamers act in an induced-fit manner, which allows them to function as a small molecule capture arm on a supported surface. We had aptamer Rd 13 tested on a GFET made by A. T. Charlie Johnson and colleagues at the University of Pennsylvania. Their particular GFET and the test are described below in Example 4. The GFET functionalized with amino-Rd13 was used to measure posaconazole concentration. Posaconazole was diluted from DMSO into modified SELEX buffer as described above. The sensor output signal was taken to be the Dirac voltage shift, measured relative to the shift induced upon exposure to pure buffer. Sensor output signal versus drug concentration is shown in FIG. 10. As the concentration of posaconazole was increased from 0.01 µg/mL to 100 µg/mL, the relative Dirac voltage shift increased to upwards of −6V. The variation of the relative Dirac voltage shift with concentration was well fit by a model based on the Langmuir-Hill theory of equilibrium binding, where the dissociation constant of the aptamer is a fitting parameter. See Lerner M B, Matsunaga F, Han G H, Hong S J, Xi J, Crook A, Perez-Aguilar J M, Park Y W, Saven J G, Liu R, Johnson A T (2014) Scalable production of highly sensitive nanosensors based on graphene functionalized with a designed G protein-coupled receptor, Nano Lett 14:2709-2714. The best fit value of 1.8±0.5 µg/mL (2.6±0.7 µM) is in good agreement with the value of 2.7±1.2 µM derived from the anisotropy assay. In a negative control experiment, treatment with the echinocandin drug caspofungin produced a negligible shift in the gate threshold voltage, providing strong evidence that the sensor response reflects specific binding of the target to the aptamer probe. As reported by the testers, the observed values of the relative Dirac voltage shift are in a range similar to that of a similarly designed aptamer-GFET biosensor biosensing for a HIV drug. The results of Example 4 reported in FIG. 10 indicate that aptamer Rd13 chemically attached to the GFET surface binds posaconazole in a similar fashion to free Rd13 aptamer in solution.

Aptamers, biosensors and methods or this invention have numerous applications. Such applications include, for example, therapeutic drug monitoring from blood or serum, quantification of drugs in other body fluids such as urine, semen, spinal fluids, sputum, saliva, bronchial washes, other respiratory fluids, and human and animal tissues. The versatility of an oligonucleotide-based biosensor, such as shown in Example 4, opens the door to numerous different applications.

Therapeutic drug monitoring requires a method of capturing molecules and separating them from a sample for analysis. Aptamers of this invention are azole drug-capturing oligonucleotides having a unique structure, which allows it to bind azole antifungal drugs. Circular Dichroism spectrophotometry (Example 3) showed that an aptamer according to this invention works as a scaffold with two sections of G-quadruplex folds. Large protein target aptamers have been made before using two, separate G-quadruplexes linked chemically to bind at separate sites. Hasegawa H, Sode K, Ikebukuro K (2008) Selection of DNA aptamers against VEGF165 using a protein competitor and the aptamer blotting method, Biotechnol Lett 30:829-834. These types of folds rarely interacted with smaller, hydrophobic molecules due to the highly charged nature of single strand DNA. When azole drugs bind to aptamers according to this invention, a structural change occurs, as shown in FIGS. 8 and 9. The CD spectra of these changes are similar to CD spectra for B→Z DNA transition. Pohl F M, Jovin T M (1972) Salt-induced co-operative conformational change of a synthetic DNA: equilibrium and kinetic studies with poly (dG-dC), J Mol Biol 67:375-396; Baker E S, Bowers M T (2007) B-DNA helix stability in a solvent-free environment, J Am Soc Mass Spectrom 18:1188-1195. The dual G-quadruplex aptamers of this invention have been proven successful for capturing small hydrophobic molecules of azole class drugs. The anisotropy binding experiments in Examples 1 and 2 show that the poly-G region is essential for target binding. When bound to the surface of a graphene field effect transistor, an aptamer of this invention works as a capture arm. As shown in Example 4, this arm collects posaconazole from the sample, which leads to a change in the GFET gate voltage. The biosensor described in Example 4 adds to the list of other aptamer-based sensing devices. Hu R, Liu T, Zhang X B, Yang Y H, Chen T, Wu C C, Liu Y, Zhu G Z, Huan S Y, Fu T, Tan W H (2015) DLISA: A DNAzyme-Based ELISA for Protein Enzyme-Free Immunoassay of Multiple Analytes, Analytical Chemistry 87:7746-7753; Liu J W, Cao Z H, Lu Y (2009) Functional Nucleic Acid Sensors, Chemical Reviews 109:1948-1998. Unlike these other types of biosensors, GFET aptamer biosensors have the potential to function without the need for secondary antibodies, fluorophores, or electrochemical mediators. See Ping J, Vishnubhotla R, Vrudhula A, Johnson A T (2016) Scalable Production of High-Sensitivity, Label-Free DNA Biosensors Based on Back-Gated Graphene Field Effect Transistors, ACS Nano 10:8700-8704. Taken together, the unique structure and binding properties of aptamers of this invention provided with a sensitive biosensor structure such as a graphene field effect transistor enable therapeutic drug monitoring.

EXAMPLES

Oligonucleotides including amino-functionalized oligonucleotides were synthesized by IDT (Coralville, Iowa, USA), Sigma-Aldrich (St. Louis, Mo., USA) and Biosearch Technologies (Novato, Calif., USA). BODIPY FL Dye was purchased from Life Technologies Co (Carlsbad, Calif., USA). Azole drugs were purchased from Santa Cruz Biotechnologies (Dallas, Tex.). All other reagents and solvents were purchased from Thermo Fisher Scientific (Waltham, Mass., USA). Modified SELEX buffer contained 140 mM sodium chloride, 2 mM potassium chloride, 5 mM magnesium chloride, 2 mM calcium chloride, in 20 mM pH 7.4 Tris Buffer)(see, Jing M, Bowser M T (2011) Methods for measuring aptamer-protein equilibria: a review, Anal Chim Acta 686:9-18). Graphene devices were fabricated using techniques described in Ping J, Vishnubhotla R, Vrudhula A, Johnson A T (2016) Scalable Production of High-Sensitivity, Label-Free DNA Biosensors Based on Back-Gated Graphene Field Effect Transistors, ACS Nano 10:8700-8704.

Example 1

Fluorescence Anisotropy Binding Experiments

Fluorescence Anisotropy experiments were conducted using a PTI Fluorometer with Fluorescence Polarizers. One hundred pmoles of posaconazole BODIPY (PosBD) was added from DMSO (1 µL) to 125 µL of modified SELEX buffer. Fluorescence anisotropy experiments were recorded using a polarizer system and the G-factor was calculated manually for each run but consistently fell within 0.44-0.45. Anisotropy measurements were recorded first for 2 minutes.

Anisotropy values were plotted as the change in anisotropy:

$$\Delta\langle r\rangle(C)=\langle r\rangle(C)-\langle r\rangle_o, \quad \text{Equation 1}$$

where $\langle r\rangle(C)$ is the anisotropy value at a given concentration of aptamer and $\langle r\rangle_o$ is the initial anisotropy value. These values were used to calculate a bound fraction:

$$F_{bound}(C) = \frac{\Delta\langle r\rangle(C)}{\Delta\langle r\rangle_{max}}, \quad \text{Equation 2}$$

where $\Delta\langle r\rangle(C)$ is the anisotropy change at a given concentration and $\Delta\langle r\rangle_{max}$ is the maximum change in anisotropy.

The bound fraction was further used to calculate a dissociation constant by fitting to:

$$F_{bound}(C) = \frac{C}{C+K_d}, \quad \text{Equation 3}$$

where C is the concentration and $K_d$ is the dissociation constant.

In a first experiment the change in anisotropy caused by varying concentration of aptamer Rd13 to BODIPY-labeled Posaconazole was determined. One hundred pmoles of Posaconazole-BODIPY (PosBD) was added from DMSO (1 µL) to 125 µL of modified SELEX buffer. After the initial 2 minutes, aliquots of the aptamer from 1 pmole to 2000 pmoles were added, and samples were equilibrated for 5 minutes. The value of the anisotropy was taken to be the average anisotropy of the last 60 seconds after equilibration. Results are presented in FIG. 2, where line 21 shows the change in anisotropy versus the concentration of aptamer Rd 13.

In a second experiment, the change in anisotropy caused by aptamer Rd 13 was determined for the BODIPY-labeled drugs posaconazole (Pos), and caspofungin (CSF). One hundred pmoles of aptamer Rd 13 were titrated into each of the labeled drugs, and the change in anisotropy was determined as described above. Results are presented in FIG. 3, where each error bar represents plus-one standard deviation.

In a third experiment, the changes in anisotropy caused by titrating 100 pmoles of aptamers Rd 13, Rd 13 T6, and Rd 13 T1 into 100 pmoles of PosBD were determined. The anisotropy changes were 0.04153, 0.031717 and 0.022733, respectively. For comparative purposes, two other molecules were included in the test along with the three aptamers: a scrambled version of Rd 13 and EDTA. Results are presented in FIG. 4. The scrambled version of aptamer Rd 13 was a molecule having the same length and the same nucleotide composition as aptamer Rd 13 but having the order of the nucleotides scrambled in such a way that there were no instances of three contiguous G's. The sequence of that molecule, "Rd 13 S", was:

```
                                           (SEQ ID NO: 7)
GCTGTGTGCGTGAGTGGAGTGCGCGCGAGAGTGAGTGCGGTGAGA

GATTC GGTGTGCGTGTCGTGATGAATGCGACCGG
```

Example 2

Fluorescence Anisotropy Competition Assays

Competition assays were performed using the same measurement techniques as described above for binding assays. In this experiment, 50 pmoles of PosBD was added from DMSO into 125 µL of modified SELEX buffer, and the anisotropy was recorded for 2 minutes. One thousand pmoles of aptamer Rd 13 was then added and allowed to equilibrate for 10 minutes. After this time, 1000 pmoles of an unlabeled drug molecule, either posaconazole (Pos), fluconazole (Flu), itraconazole (Itra), or voficonazole (Vori), was added and the solution was heated up to 70° C. for 3 minutes and cooled on ice for 2 minutes. The heat-ice cycle was performed twice. The anisotropy was then recorded again for another 5 minutes. The percent of PosBD replaced by each unlabeled drug was calculated as:

$$\% \text{ Replaced} = 100 * \frac{\langle r\rangle_{aptamer,drug} - \langle r\rangle_0}{\langle r\rangle_{aptamer} - \langle r\rangle_0}, \quad \text{Equation 4}$$

where $\langle r\rangle_{aptamer}$ is anisotropy with addition of the aptamer only and $\langle r\rangle_{aptamer,drug}$ is the final anisotropy value after addition of the new drug. Percent replaced equals 100 multiplied by the anisotropy with aptamer and drug replacement minus the initial anisotropy divided by the anisotropy caused by the aptamer alone minus the initial anisotropy. For each of the four unlabeled drugs, the percent of PosBD that was replaced is shown in FIG. 5.

Example 3

Circular Dichroism Assays

Experiments were performed using an Aviv Model 420 CD Spectrophotometer. All aptamer samples were prepared at 10 µM concentration in 20 mM Tris buffer pH 7.4. Samples were placed in a 1 mm path length cuvette and scanned at 25° C. from 300 nm to 200 nm with 1 nm steps and 1 second averaging time. Circular dichroism results were calculated as the molar ellipticity (deg. cm2/dmol).

In a first experiment, differing amounts (0 to 5 mM) of magnesium chloride were added to samples containing aptamer Rd 13 but no drug molecule. Results are presented in FIG. 6, where lines 61-63 are the scans for 0 mM (Tris only), 0.5 mM, and, 1 mM magnesium chloride, respectively.

In a second experiment, differing amounts (0 to 50 µM) of posaconazole were added to samples containing aptamer Rd 13 but no Magnesium chloride. Results are presented in FIG. 7, where line 71 is the scan with no posaconazole (Tris only), line 72 is the scan for 0.5 µM posaconazole, and line 73 is the scan for 1 µM posaconazole.

In a third experiment, 0.2 mM magnesium chloride was added to samples containing either aptamer Rd 13 or the scrambled version of Rd 13. Results are presented in FIG. 8, where line 81 is the scan for aptamer Rd 13 and line 82 is the scan for molecule Rd 13 S.

In a fourth experiment, 0.2 mM magnesium chloride and 100 µM posaconazole were added to samples containing either aptamer Rd 13 or the scrambled version of Rd 13. Results are presented in FIG. 9, where line 91 is the scan for aptamer Rd 13 and line 92 is the scan for molecule Rd 13 S.

Example 4

Quantitative Detection of Drug Concentration with a Biosensor

Aptamer Rd 13 was chemically attached to the surface of a grapheme field effect transistor (GFET) to produce a biosensor. The GFET that had been incubated with 1-Pyrenylbutyric acid N-hydroxysuccinimide ester (P-base) was incubated in a solution of PBS (pH 7.6) containing amino-Rd 13 aptamer for three hours, followed by heating at 70-90° C. for 15 min and ambient cooling to room temperature.

The resulting GFET-based biosensor was used to measure posaconazole concentration. Posaconazole was diluted from DMSO into modified SELEX buffer to achieve concentrations of 0.01 µg/mL ($10^{-8}$ g/mL), 0.1 µg/mL ($10^{-7}$ g/mL), 1 µg/mL ($10^{-6}$ g/mL), 10 µg/mL ($10^{-5}$ g/mL), and 100 µg/mL ($10^{-4}$ g/mL). The biosensor was contacted with the posaconazole solutions and with pure buffer. The Dirac voltage was detected. Biosensor output signal with each posaconazole solution was determined as the Dirac voltage shift relative to the Dirac voltage shift with pure buffer. Results are presented in FIG. 10, line 101. As a control, the biosensor was also contacted with caspofungin at a concentration of 100 µg/mL ($10^{-4}$ g/mL), and the Dirac voltage shift is included in FIG. 10, data point 102.

Example 5

Quickly and Accurately Monitoring Free-Drug Concentrations of Posaconazole and Itraconazole The azole class of antifungal drugs is an important target for the development of TDM. Better methods are needed to reach the full potential of TDM for studying drugs like posaconazole. Our assay has expanded the repertoire of existing methods by adding a way to quickly detect posaconazole concentrations in 10% serum solutions in 1 hour or less from several drops of blood. When adjusted for dilution, the concentration dynamic range is 0.224 µg/mL to ~28 µg/mL, almost 100-fold. Previous reports have noted that trough concentrations for treating azole-susceptible Aspergillus are around 0.2 µM and that therapeutic concentrations for other invasive infections can be upwards of 1.5 µM (Andes, D.; Pascual, A.; Marchetti, O., Antifungal Therapeutic Drug Monitoring: Established and Emerging Indications. Antimicrob Agents Ch 2009, 53 (1), 24-34; Dekkers, B. G. J.; Bakker, M.; van der Elst, K. C. M.; Sturkenboom, M. G. G.; Veringa, A.; Span, L. F. R.; Alffenaar, J. C., Therapeutic Drug Monitoring of Posaconazole: an Update. Current fungal infection reports 2016, 10, 51-61). Peak concentrations may even reach the higher end of our dynamic range, making this assay extremely useful to clinicians. The assay is highly specific as only posaconazole and itraconazole caused significant signals along with isavuconazole to a lesser extent. This assay can be combined with other analytical and bioassay techniques. The assays described herein serve as a method to individually monitor the concentration of different azole drugs when used in combination therapies. The reduced Graphene Oxide-aptamer assay as described herein provides a new, important diagnostic tool for improving TDM of certain azole class antifungal drugs.

RESULTS

Assay for Posaconazole in Buffer and Serum

Figure 12:
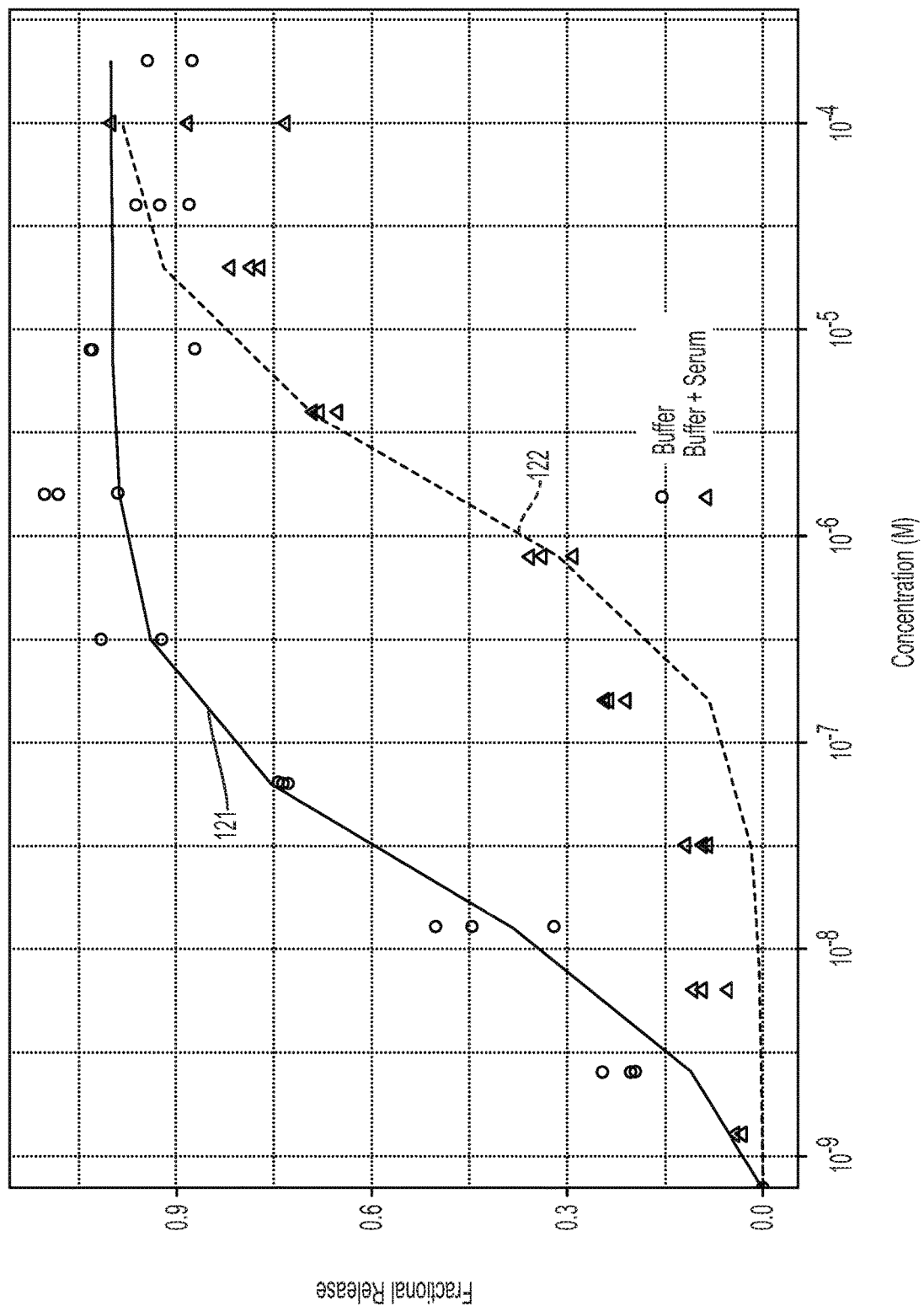
FIG. 12 is a graph showing results from a rGO assay in SELEX buffer and 10% Human Serum. Posaconazole was spiked into SELEX buffer with and without 10% Human Serum. The change in fluorescein signal was taken to be aptamer released from the surface. Values of fractional release were calculated with respect to the minimum value (with only DMSO) and the maximum value (greatest change in fluorescence). The concentration dynamic range shifts in serum as expected due high posaconazole protein-binding.

The rGO-aptamer assay showed a detectable response when tested on samples of posaconazole in SELEX buffer and 10% serum in 100 µL total volume. Samples spiked with different amounts of posaconazole showed increasing fluorescence intensity with increasing posaconazole concentration (FIG. 12). These data were fit to a first-order reaction equation (Equation 5) as denoted by 121 and 122. Assuming that the maximum release occurred at 8 µM posaconazole, the dissociation constant was found to be 20 nM. Samples in 50% serum suffered from significant signal-to-noise issues as the minimum detectable concentration was at 5 µM. The samples tested in 10% serum caused a better response. The dissociation constant for posaconazole in 10% serum was found to be 1.7 µM, almost 100-fold higher than in SELEX buffer. These results are in line with the hypothesis that posaconazole is upwards of 99% protein bound in human serum; the assay detects free drug in serum. A dynamic range of detection in 10% serum was determined to be 0.224 µM to 28 µM.

Selectivity of Posaconazole Assay

The selectivity of the posaconazole assay was examined against the other azole class antifungal drugs. Interestingly, in SELEX buffer only Isavuconazole and Itraconazole were able to liberate aptamer from the rGO surface and cause an increase in fluorescence FIGS. 13(A) and 13(B). Two control tests were performed to examine chemical specificity. The highly hydrophobic antifungal drug Amphotericin B did not cause a significant signal in this assay in SELEX buffer. Additionally, a single benzene ring molecule Para-aminobenzoic acid (PABA) was unable to cause aptamer release from the surface. Taken together these data highlight the fact that the assay is not simply influenced by hydrophobicity (Amp B) or a simple structural characteristic (PABA).

Assay for Itraconazole and Isavuconazole in 10% Serum

Figure 14:
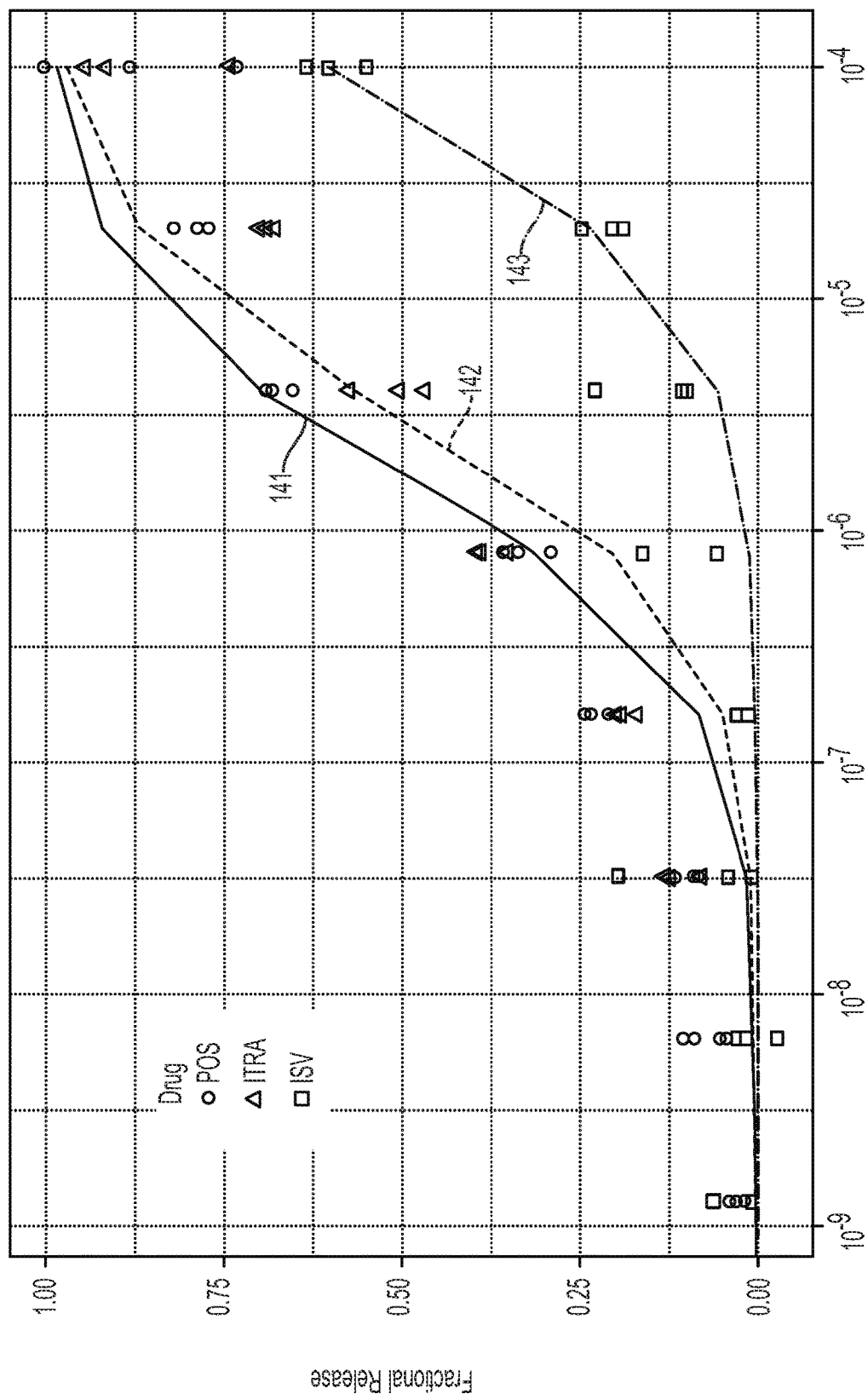
FIG. 14 is a graph showing a comparison of Aptamer release with Azoles. Samples of SELEX buffer+10% Serum were spiked with three azole class drugs posaconazole, itraconazole, and isavuconazole. The assay showed increased sensitivity towards posaconazole and itraconazole relative to that of isavuconazole.

We examined the ability of this assay to detect itraconazole and isavuconazole in 10% serum solutions. The apparent detection limit for itraconazole appeared to be the same as posaconazole: 0.224 µM. The apparent detection limit for Isavuconazole, however, appeared to be greater at above 1.12 µM. Fitting to a first-order reaction equation was done by taking a control well of 100 µM posaconazole to be the maximum release. The dissociation constants for itraconazole and isavuconazole were found to be, respectively: 3 µM and 65 µM in 10% serum from fits along with a fit to posaconazole in 141, 142, 143 for posaconazole, itraconazole, and isavuconazole respectively. FIG. 14. The value for itraconazole was in the range of that found for posaconazole but isavuconazole was almost 40 times higher. Taken together these data show the utility of this assay in detecting posaconazole and itraconazole in serum solutions.

Assay for Posaconazole in Blood Samples

Figure 15:
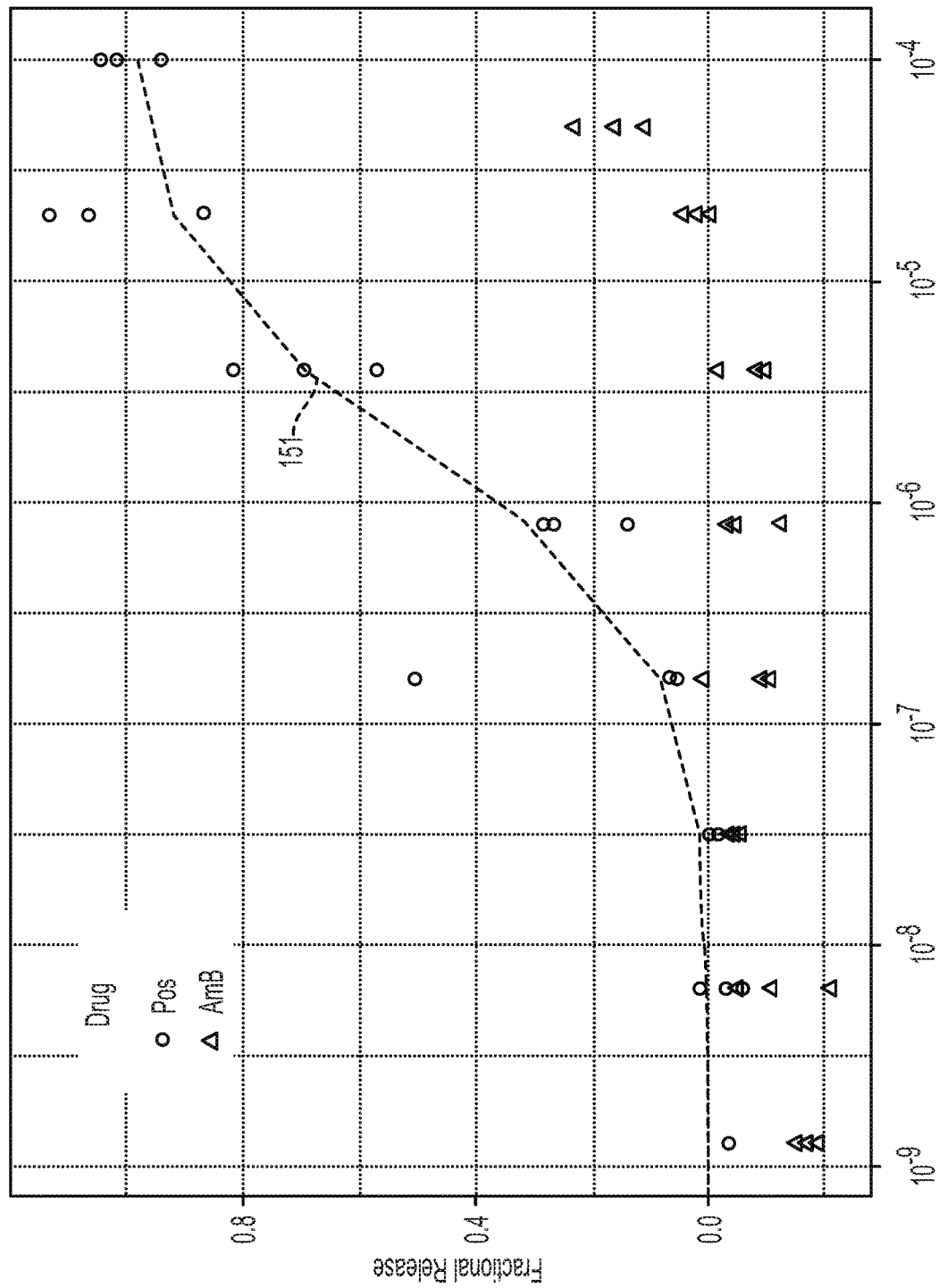
FIG. 15 is a graph showing aptamer release in spiked whole blood samples. Samples of Sheep Blood were diluted to 10% in SELEX buffer and spiked with either posaconazole or amphotericin B. The detectable concentration range (fractional release) for posaconazole was similar to that observed in human serum. Amphotericin B caused little detectable signal relative to the signal caused by posaconazole.

We tested the rGO-aptamer assay in samples of Sheep's blood spiked with posaconazole. The detection limit when adjusting for the assay in this media, after adjusting for dilution, was 0.224 µg/mL with an upper limit of 140 µg/mL FIG. 15. The maximum fractional release for these data were determined relative to the maximum fluorescence change observed in the experiment at a posconazole concentration of between 10 µM to 100 µM with fitting to Equation 5 denoted in 151. Comparatively, there was little to no signal generated in blood samples spiked with Amphotericin B. These values were in line with measurements conducted in serum and again showed a similar shift in detection limit relative to samples in 100% buffer. The rGO-aptamer assay, therefore, can be used in a variety of media including blood serum and whole blood.

MATERIAL AND METHODS

Reagents

Human Serum and posaconazole were purchased from Sigma Aldrich (St. Louis, Mo.). Fluconazole and other azole drugs were purchased from Santa Cruz Biotechnologies (Dallas, Tex.). rGO was purchased from Graphenea (San Sebastián, Spain). Fluorescein-labeled aptamers were synthesized by LGC Biosearch Technologies (Petaluma, Calif.). All other reagents and solvents were purchased from Thermo Fisher Scientific (Waltham, Mass.).

Preparing rGO-Aptamer Mixtures

Samples were made by first solubilizing 30 nmols of Fluorescein-labeled aptamer in 1× SELEX buffer (14 mM Sodium Chloride, 0.2 mM Potassium Chloride, 0.5 mM Magnesium Chloride, 0.2 mM Calcium Chloride in 2 mM pH 7.4 Tris). The DNA was then heated at 95° C. for 5 minutes, placed on ice for 15 minutes, and then incubated at room temperature (25° C.) for 5 minutes. A stock solution of 1 mg/mL rGO as prepared in either 1× SELEX buffer or 1× SELEX buffer with 10% human serum. The DNA was incubated with 150 µL of the 1 mg/mL rGO for 15 minutes at room temperature with shaking. The sample was then spun down at 5000 g for 1 minute. The supernatant was removed and the graphene pellet was washed once with either 1× SELEX buffer or 1× SELEX buffer with 10% human serum.

Fluorescence Assay

The fluorescence assays in this work were conducted in 96-well Sarstedt plates (Nümbrecht, Germany). Dilutions of azole drugs were prepared in DMSO and pipetted individually into well of the plates. The amount of DMSO was a constant 1 µL; after this 50 µL of buffer (SELEX or SELEX with 10% serum) was added to each well. Samples of rGO that had been incubated with aptamer and washed were solubilized into 1.5 mL of the appropriate buffer. Then, 50 µL of this sample was pipetted into one of 30 wells. The ratio of graphene:well was set to 5 µL of 1 mg/mL graphene per well.

Samples were then allowed to incubate for up to one hour. After one hour, the plates were placed into a Tecan infinite M200Pro plate reader. The samples were read in fluorescence mode with an excitation at 494 nm and an emission at 525 nm. Sample fluorescence values were analyzed in Microsoft Excel and R. These values were normalized to a background well containing only 1 µL of DMSO and a maximum control well containing 100 µM Posaconazole. Data curves were fit to a standard first order reaction equation:

$$F_r(C) = \frac{C}{C + k_d} \qquad \text{Equation 5}$$

Where the Fraction released ($F_r$) with respect to Concentration (C) is a function of the concentration and the dissociation constant $k_d$.

The foregoing examples are only embodiments of the aptamers, biosensors and methods of this invention. Various modifications and alterations to the described embodiments will be apparent to those skilled in the art in view of the inventors' teachings herein. Such modifications and alterations will be within the spirit of the invention and scope of the appended claims. Therefore, the above-described examples should be considered is a descriptive sense only and not for purposes of limitation.

What is claimed is:

1. A DNA aptamer that has a G-quadruplex structure, that binds specifically to the azole class antifungal drugs posaconazole, fluconazole, isavuconazole, voriconazole and itraconazole, and that has a nucleotide sequence consisting essentially of the following regions: a first conserved region consisting essentially of SEQ ID NO: 1, a variable connector region of at least one nucleotide, a second conserved region consisting essentially of SEQ ID NO: 2, and a variable 3' terminal region of 0-10 nucleotides, said aptamer having a binding affinity for posaconazole of at least 50% of the binding affinity of aptamer SEQ ID NO: 4 as determined by a change in anisotropy upon titration of 100 pmoles of aptamer into 100 pmoles of BODIPY-labeled posaconazole.

2. The DNA aptamer of claim 1, wherein the connector region consists essentially of SEQ ID NO: 3 or a subsequence thereof.

3. The DNA aptamer of claim 1, wherein the connector region is selected from the group consisting of SEQ ID NO: 3, GCTTGA, and thymine (T).

4. The DNA aptamer of claim 1, wherein the 3' terminal region consists essentially of TGCCTG or a subsequence thereof.

5. The DNA aptamer of claim 1 having the nucleotide sequence of SEQ ID NO: 4.

6. A biosensor for azole class antifungal drugs posaconazole, fluconazole, voriconazole and itraconazole comprising an aptamer according to claim 1 and a material having a surface to which the aptamer is attached.

7. The biosensor according to claim 6, wherein the material is graphene oxide, reduced graphene oxide, or a graphene derivative.

8. A method for determining the level in a biological sample of an azole class antifungal drug from the group consisting of posaconazole, fluconazole, isavuconazole, voriconazole and itraconazole comprising the steps of contacting the sample with an aptamer or biosensor of any of the preceding claims and detecting the level of binding of the aptamer to the drug.

9. The method of claim 8, wherein the level of binding that is detected is the amount of aptamer that is bound to the drug.

10. The method of claim 8, wherein the level of binding that is detected is the binding strength of the aptamer to the drug.

11. The biosensor of claim 6, comprising a graphene field effect transistor (GFET) having an aptamer according to claim 1 fixed to its surface by a linker.

* * * * *

SEQUENCE LISTING

<160> NUMBER OF SEQ ID NOS: 8

<210> SEQ ID NO 1
<211> LENGTH: 26
<212> TYPE: DNA
<213> ORGANISM: ARTIFICIAL SEQUENCE
<220> FEATURE:
<223> OTHER INFORMATION: Synthetic construct

<400> SEQUENCE: 1 cgggggagg cggagggagg actggg                    26

```
<210> SEQ ID NO 2
<211> LENGTH: 23
<212> TYPE: DNA
<213> ORGANISM: ARTIFICIAL SEQUENCE
<220> FEATURE:
<223> OTHER INFORMATION: Synthetic construct

<400> SEQUENCE: 2
ggggtaaggg cttaggtggt tgg                                           23

<210> SEQ ID NO 3
<211> LENGTH: 24
<212> TYPE: DNA
<213> ORGANISM: ARTIFICIAL SEQUENCE
<220> FEATURE:
<223> OTHER INFORMATION: Synthetic construct

<400> SEQUENCE: 3
gcttcattga cgttcttcac agta                                          24

<210> SEQ ID NO 4
<211> LENGTH: 79
<212> TYPE: DNA
<213> ORGANISM: ARTIFICIAL SEQUENCE
<220> FEATURE:
<223> OTHER INFORMATION: Synthetic construct

<400> SEQUENCE: 4 cgggggagg cggagggagg actggggctt cattgacgtt cttcacagta ggggtaaggg    60
cttaggtggt tggtgcctg                                                79

<210> SEQ ID NO 5
<211> LENGTH: 61
<212> TYPE: DNA
<213> ORGANISM: ARTIFICIAL SEQUENCE
<220> FEATURE:
<223> OTHER INFORMATION: Synthetic construct

<400> SEQUENCE: 5 cgggggagg cggagggagg actggggctt gagggtaag gcttaggtg gttggtgcct      60 g                                                                   61

<210> SEQ ID NO 6
<211> LENGTH: 56
<212> TYPE: DNA
<213> ORGANISM: ARTIFICIAL SEQUENCE
<220> FEATURE:
<223> OTHER INFORMATION: Synthetic construct

<400> SEQUENCE: 6 cgggggagg cggagggagg actgggtggg gtaagggctt aggtggttgg tgcctg        56

<210> SEQ ID NO 7
<211> LENGTH: 79
<212> TYPE: DNA
<213> ORGANISM: ARTIFICIAL SEQUENCE
<220> FEATURE:
<223> OTHER INFORMATION: Synthetic construct

<400> SEQUENCE: 7
gctgtgtgcg tgagtggagt gcgcgcgaga gtgagtgcgg tgagagattc ggtgtgcgtg   60
tcgtgatgaa tgcgaccgg                                                79

<210> SEQ ID NO 8
```

```
<211> LENGTH: 79
<212> TYPE: DNA
<213> ORGANISM: ARTIFICIAL SEQUENCE
<220> FEATURE:
<223> OTHER INFORMATION: Synthetic construct
<220> FEATURE:
<221> NAME/KEY: misc_feature
<222> LOCATION: (27)..(50)
<223> OTHER INFORMATION: n can be a, c, g or t and up to 24 of these can
      be absent.
<220> FEATURE:
<221> NAME/KEY: misc_feature
<222> LOCATION: (74)..(79)
<223> OTHER INFORMATION: n can be a, c, g or t and up to 6 of these can
      be absent.

<400> SEQUENCE: 8 cgggggggagg cggagggagg actgggnnnn nnnnnnnnnn nnnnnnnnnn ggggtaaggg      60
cttaggtggt tggnnnnnn                                                    79
```